US009250239B2

(12) United States Patent
Garg

(10) Patent No.: US 9,250,239 B2
(45) Date of Patent: Feb. 2, 2016

(54) COMPOSITIONS AND METHODS FOR DETECTING MICROBIAL INFECTIONS

(71) Applicant: Nisha J. Garg, League City, TX (US)

(72) Inventor: Nisha J. Garg, League City, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/175,001

(22) Filed: Feb. 7, 2014

(65) Prior Publication Data

US 2014/0220603 A1    Aug. 7, 2014

Related U.S. Application Data

(60) Division of application No. 13/135,621, filed on Jul. 11, 2011, now Pat. No. 8,663,649, which is a continuation-in-part of application No. PCT/US2010/002465, filed on Sep. 10, 2010.

(60) Provisional application No. 61/276,274, filed on Sep. 10, 2009.

(51) Int. Cl.
*G01N 33/53* (2006.01)
*G01N 33/569* (2006.01)
(Continued)

(52) U.S. Cl.
CPC ........ *G01N 33/56905* (2013.01); *A61K 39/005* (2013.01); *A61K 2039/53* (2013.01); *A61K 2039/55522* (2013.01); *A61K 2039/55538* (2013.01); *A61K 2039/55577* (2013.01)

(58) Field of Classification Search
CPC .............................. C12Q 1/6809; G01N 33/53
USPC ........................ 435/7.2, 7.23, 7.22, 7.31, 7.92
See application file for complete search history.

(56) References Cited

U.S. PATENT DOCUMENTS 3,911,097 A * 10/1975 Hanson ...................... 424/269.1
3,993,743 A * 11/1976 Hanson ......................... 435/7.22
(Continued)

FOREIGN PATENT DOCUMENTS

WO    WO 2009-056965 A2    5/2009

OTHER PUBLICATIONS

Kaplan, Dan et al, PNAS, USA, vol. 94, pp. 10301-10306, Sep. 1997, Antibodies to Ribosomal P proteins of Trypanosoma cruzi in Chagas disease possess functional autoreactivity with heart tissue and differ from anti-P autoantibodies in lupus.*
(Continued)

*Primary Examiner* — Albert Navarro
*Assistant Examiner* — Ginny Portner
(74) *Attorney, Agent, or Firm* — Norton Rose Fulbright US LLP

(57) ABSTRACT

Provided herein are vaccine compositions for control of *Trypanosoma cruzi* infection and Chagas disease. The compositions comprise plasmids encoding o GPI-anchored genes ASP-2, TcG-1, TcG2 and TcG4 from *Trypanosoma cruzi*; plasmids encoding cytokines IL12 and GM-CSF; and plasmids encoding a gene expression system. Certain vaccine compositions comprise recombinant proteins, selected from TcG-1, TcG2 and TcG4 from *Trypanosoma cruzi*. In another vaccination strategy, the recombinant proteins are replaced by lysates comprising *Trypanosoma rangeli* cells. Further provided herein are diagnosis compositions comprising 1) recombinant proteins, selected from TcG-1, TcG2 and TcG4 from *Trypanosoma cruzi*; 2) antibodies that specifically binds the TcG-1, TcG2 and TcG4 proteins; 3) sense and antisense polynucleotide sequences that encode the TcG-1, TcG2 and TcG4 proteins. Said compositions can be used in diagnosing and/or evaluating efficacy of treatments against *Trypanosoma cruzi* infection. A diagnosis kit, and methods of diagnosing and/or treating *Trypanosoma cruzi* infection are also provided.

8 Claims, 12 Drawing Sheets

(51) Int. Cl.
*A61K 39/005* (2006.01)
*A61K 39/00* (2006.01)

(56) References Cited

U.S. PATENT DOCUMENTS

| | | | | |
|---|---|---|---|---|
| 4,870,006 | A * | 9/1989 | Dragon et al. | 435/7.22 |
| 5,550,027 | A * | 8/1996 | Winkler et al. | 435/7.22 |
| 6,015,662 | A * | 1/2000 | Hackett et al. | 435/5 |
| 6,228,601 | B1 * | 5/2001 | Kirchhoff et al. | 435/7.22 |
| 6,682,900 | B1 * | 1/2004 | Travassos et al. | 435/7.22 |
| 6,875,584 | B1 * | 4/2005 | Tarleton et al. | 435/69.1 |
| 7,309,784 | B2 * | 12/2007 | Tarleton et al. | 536/23.7 |
| 7,888,135 | B2 * | 2/2011 | Tarleton et al. | 436/518 |
| 8,329,411 | B2 * | 12/2012 | Tarleton et al. | 435/7.1 |
| 2003/0108960 | A1 * | 6/2003 | Zrein | 435/7.22 |
| 2005/0158347 | A1 * | 7/2005 | Tarleton et al. | 424/269.1 |
| 2007/0178100 | A1 * | 8/2007 | Tarleton | 424/151.1 |
| 2008/0019995 | A1 * | 1/2008 | Tarleton et al. | 424/191.1 |
| 2008/0096232 | A1 * | 4/2008 | Shah et al. | 435/7.22 |
| 2010/0323909 | A1 * | 12/2010 | Tarleton et al. | 506/9 |
| 2011/0038887 | A1 * | 2/2011 | Contreras | A61K 38/16 424/191.1 |
| 2011/0280901 | A1 * | 11/2011 | Garg | 424/191.1 |
| 2012/0316209 | A1 * | 12/2012 | Tarleton et al. | 514/386 |
| 2013/0224249 | A1 * | 8/2013 | Filho et al. | 424/269.1 |

OTHER PUBLICATIONS

Ayub, M. J. et al, Gene, vol. 357, 2005, pp. 129-135, Protein-protein interaction map of the Trypanosoma cruzi ribosomal P protein complex.*
Bonfa, E. et al, The Journal of Immunology, vol. 150, pp. 3917-3923, May 1, 1993, Autoantibodies in Chagas' Disease.*
Bhatia, V et al, Clinical and Vaccine Immunology, Aug. 2008, vol. 15(8), pp. 1158-1164, Previously unrecognized Vaccine Candidates Control Trypanosoma cruzi Infection and Immunopathology in Mice.*
Silveira, Eduardo L V. et al, Clinical and Vaccine Immunology, Aug. 2008, vol. 15(8) pp. 1292-1300, Novel Protective Antigens Expressed by Trypanosoma cruzi Amastigotes Provide Immunity to Mice Highly Susceptible to Chaga' Disease.*
Garg, Nisha et al, The Journal of Biological Chemistry, vol. 272(19), May 9, 1997, 12482-12491, Proteins with Glycosylphosphatidylinositol (GPI) Signal Sequences Have Divergent Fates During a GPI Deficiency.*
Umezawa, Eufrosina S. et al, Journal of Clinical Microbiology, Sep. 1996, pp. 2143-2147, vol. 34(9) Immunoblot Assay Using Excreted-Secreted Antigens of Trypanosoma cruzi in serodiagnosis of congenital Acute and Chronic Chagas' Disease.*
Bhatia, V et al, Infection and Immunity, Nov. 2004, pp. 6245-6254, vol. 72(11), Utility of the Trypanosoma cruzi Sequence database for Identification of Potential Vaccine Candidates by In Silico and In Vitro Screening.*
Aparicio-Burgos, Jose E., et al., "Testing the Efficacy of a Multi-Component DNA-Prime/DNA-Boost Vaccine against Trypanosma cruzi infection in Dogs", PLOS Neglected Tropical Diseases, May 2011, pp. 1-10, vol. 5(5).
Barnabe et al., Exp Parasitol, 2001, 99, 73-79.
Barr et al., Am J Vet Res, 1995, 56, 1037-1044.
Beard et al., J Parasitol, 1988, 343-344.
Bern et al., Clin Infect Dis, 2009, 49, e52-54.
Bhatia et al., Infect Immun, 2004, 72, 6245-6254.
Bhatia et al., Clin Vaccine Immunol, 2008, 15, 1158-1164.
Bradley et al., J Am Vet Med Assoc, 2000, 217, 1853-1857.
CDC, MMWR Morb Mortal Wkly Rep, 2006, 55, 798-800.
CDC, MMWR Morb Mortal Wkly Rep, 2007, 56, 141-143.
Cohen et al., Science, 2001, 293, 695-698.
Garg et al., J Immunol, 1997, 158, 3293-3302.
Garg et al., In: Proceedings 10th International Congress of Immunology, New Delhi, India, 1998, 1421-1426.
Garg et al., Infection & Immunity, 2002, 70, 5547-5555.
Garraud et al., Travel Med Infect Dis, 2007, 5, 110-112.
Gupta, Shivali, et al., Prophylactic Efficacy of TcVac2 against Trypanosoma cruzi in Mice, PLOS Neglected Tropical Diseases, Aug. 2010, pp. 1-8, vol. 4(8).
Gurtler et al., Ann Trop Med Parasitol, 1990, 84, 313-323.
Gurtler et al., Am J Trop Med Hyg, 1996, 55, 24-31.
Gurtler et al., J Appl Ecol, 1997, 34, 699-715.
Guzman-Bracho C., Trends Parasitol, 2001, 17, 372-376.
Low et al., J Immunol, 1998, 160, 1817-1823.
Meurs et al., J Am Vet Med Assoc, 1998, 213, 497-500.
Moncayo A., Mem Inst Oswaldo Cruz, 98, 577-591.
Rodriques-Coura et al., Mem Inst Oswaldo Cruz, 2002, 97, 3-24.
Schofield et al., Trends Parasitol, 22, 583-588.
Sepulveda et al., Infect Immun, 2000, 68, 4986-4991.
Umekita et al., Braz J Med Biol Res, 2000, 33, 253-258.
Weinburg et al., Emerg Infect Dis, 2003, 9, 97-102.
Wizel et al., J Immunol, 1997, 159, 6120-6130.
Wizel et al., Infect Immun, 1998, 66, 5073-5081.

* cited by examiner

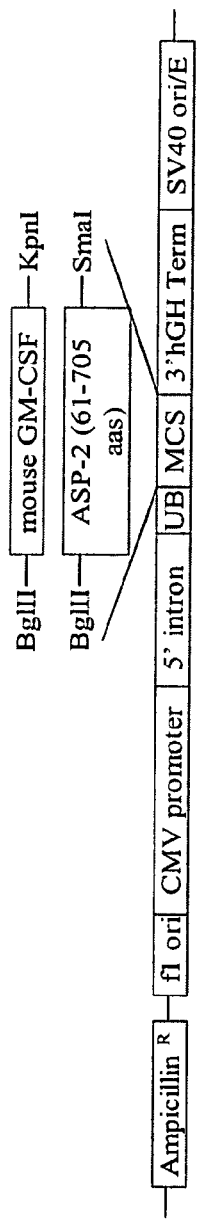
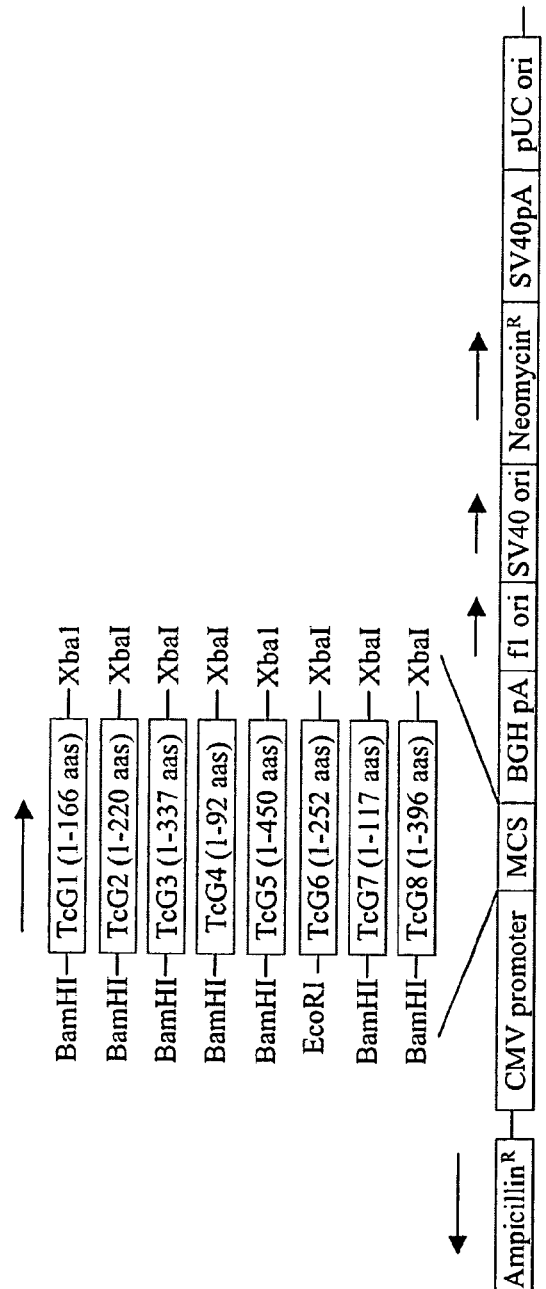
FIG. 2A
FIG. 2B

Amplification of TcG1-TcG8 for cloning in pCDNA3.1

| | SEQ ID NO: | | | SEQ ID NO: | |
|---|---|---|---|---|---|
| TcG1 | 10 | GGATCCATGGTGAAGGCGAACTATATT | GGGTCTAGATCACGTTCGAGATGCGCTTC | 11 | 499 |
| TcG2 | 12 | GGATCCATGTGCTTTCATTATCGAGTCAGGG | GGGTCTAGATCACCCAACAGCGGTGAA | 13 | 662 |
| TcG3 | 14 | GGATCCATGCTCTTCAGCGTACCTGCAGC | GGGTCTAGATCAGCTTGACACTTCGC | 15 | 1011 |
| TcG4 | 16 | GGATCCATGTCAGCCAAGGCTCCC | GGGTCTAGATCACTTTCAAGCGCC | 17 | 276 |
| TcG5 | 18 | GGATCCATGGGGAAGGAAAAAGGTGC | GGGTCTAGATCACTTCTTAGCGGC | 19 | 1350 |
| TcG6 | 20 | AAGGCTATGCTGGCGACAC | GGGTCTAGATCACACAGCAAGGG | 21 | 756 |
| TcG7 | 22 | GGATCCATGCTGGGCGACACACGG | GGGTCTAGACTACATCCATCCTCGCC | 23 | 351 |
| TcG8 | 24 | GGATCCATGTCCGATAACCATCAACTGG | GGGTCTAGA TCACTGTGGTACAACGCTG | 25 | 1188 |
| TcGPI8 | 26 | AAGCTTCGAGCATTGTCTATGTGCCTTGAA | CTCGAGCTACAGCAGGTCATATTGTACATC | 27 | 450 |

Underlined sequences represent restriction sites

FIG. 2C

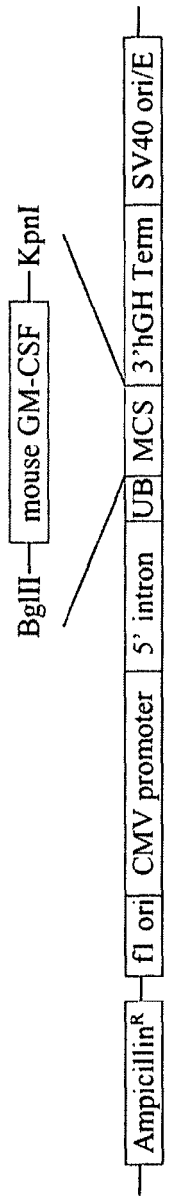

CMV1.UBF3/2 encoding GM-CSF (mouse)

FIG. 2D

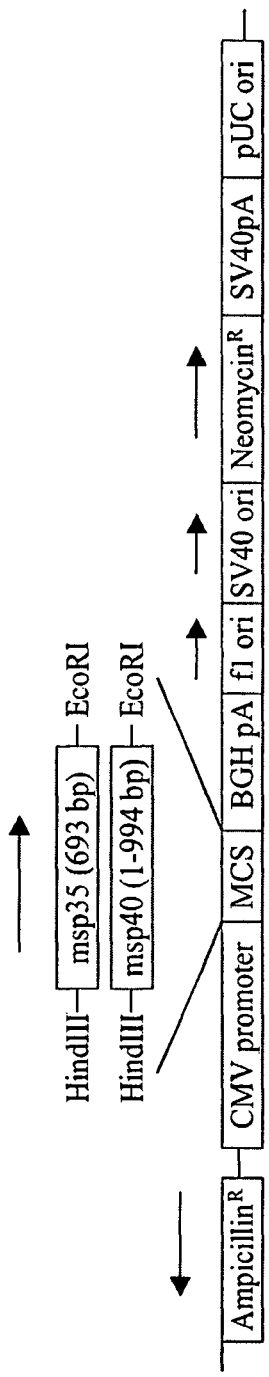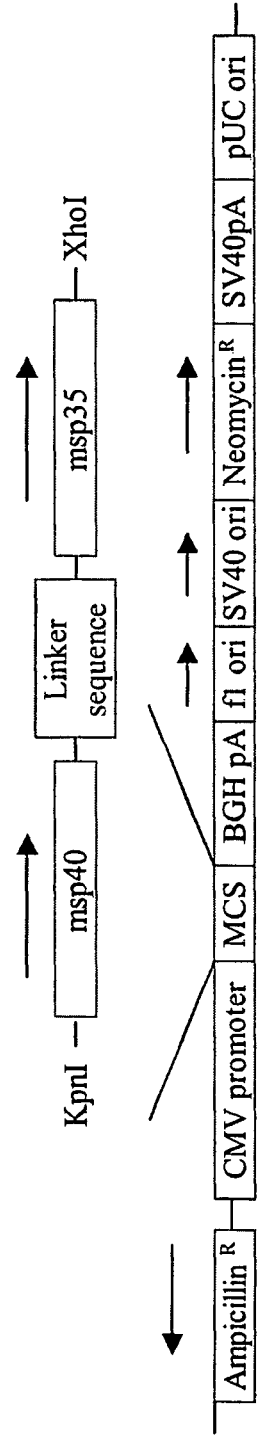

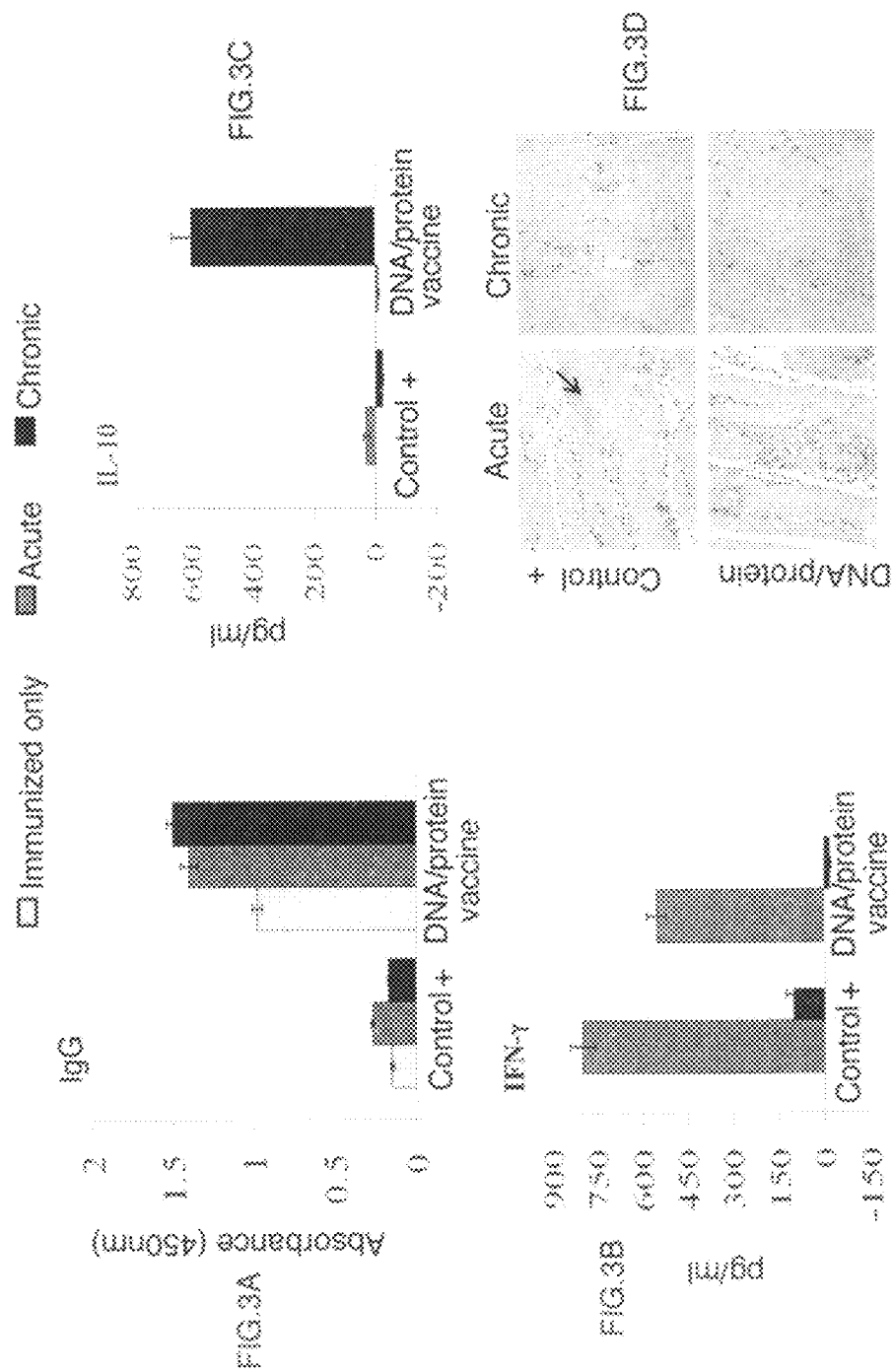

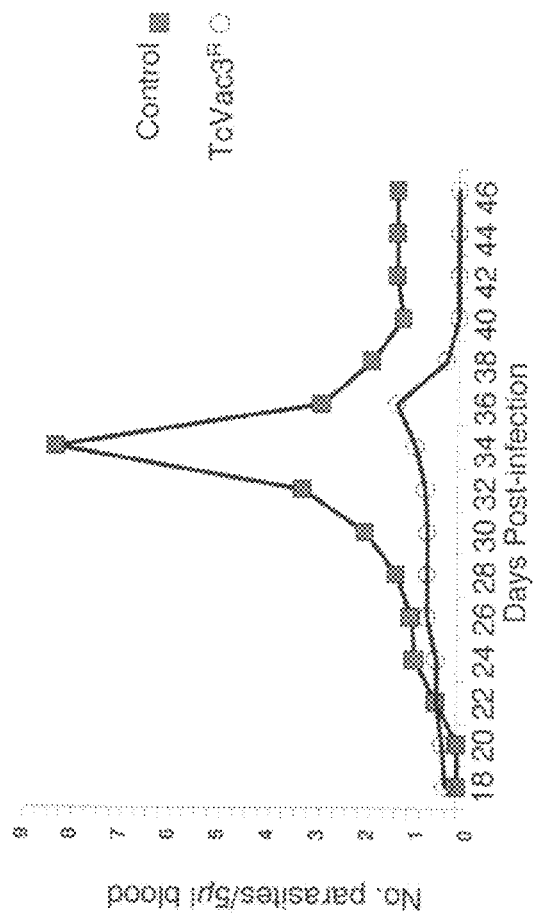
FIG. 5A
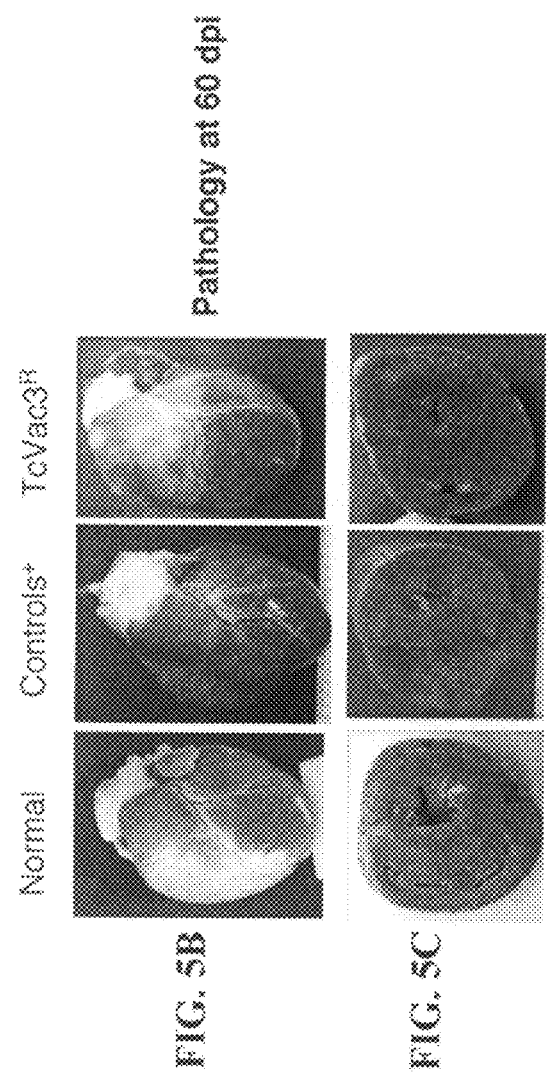
FIG. 5B
FIG. 5C

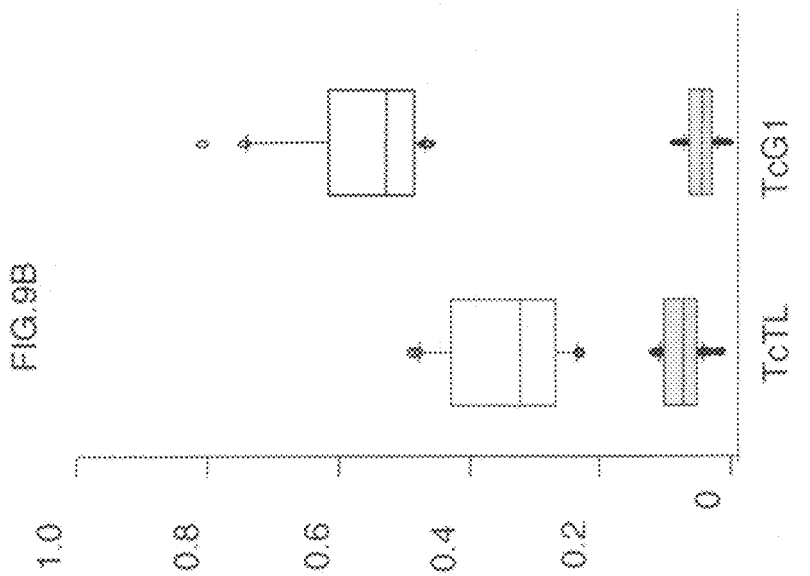
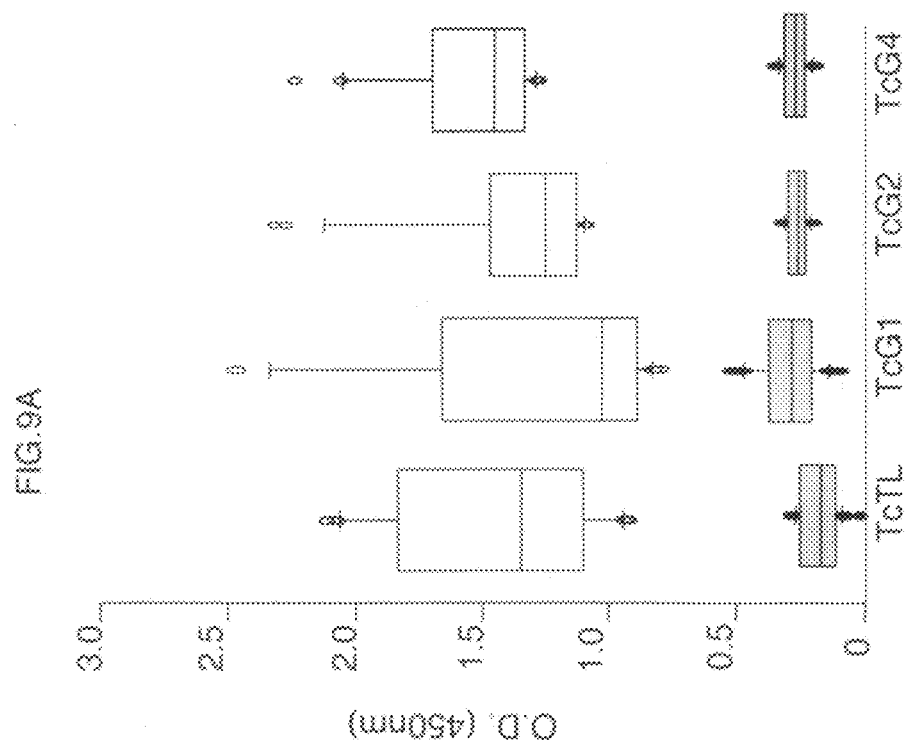

COMPOSITIONS AND METHODS FOR DETECTING MICROBIAL INFECTIONS

CROSS-REFERENCE TO RELATED APPLICATIONS

This application is a divisional application of U.S. application Ser. No. 13/135,621 filed Jul. 11, 2011 (pending), which is a continuation-in-part application claiming benefit of priority under 35 U.S.C. §120 of pending international application PCT/US2010/002465, filed Sep. 10, 2010 (expired), which claims benefit of priority under 35 U.S.C. §119(e) of provisional application U.S. Ser. No. 61/276,274, filed Sep. 10, 2009. Priority is claimed to each application described above and each application is hereby incorporated by reference in its entirety.

FEDERAL FUNDING

The invention was supported by Grant No. R03A1072538 awarded by the National Institutes of Health. Consequently, the Government has certain rights in the invention.

BACKGROUND OF THE INVENTION

1. Field of the Invention

The present invention relates to the field of human and animal health and in particular to vaccination approaches for control of *Trypanosoma cruzi* infection and Chagas disease. The present invention also relates to diagnosis of *Trypanosoma cruzi* infection and provides composition and methods for detecting *Trypanosoma cruzi* infection and evaluating efficacy of treatments against *T. cruzi*.

2. Description of the Related Art

American trypanosomiasis or Chagas disease caused by *Trypanosoma cruzi* infection is the prime cause of death in young adults in endemic areas of the American continent and results in over 50,000 deaths, 1 million new cases, and loss of 2.74 million disability-adjusted years per year.

The prevalence rate of *T. cruzi* infection in dogs may reach up to 84%, determined by serological procedures and xenodiagnosis, in endemic areas (e.g. rural Argentina, Chiapas state of Mexico) [1, 2]. Dogs are the most frequent blood meal source for the domestic triatomines (*T. barberi* and *T. pallidipennis* in Mexico [3], *T. infestans* in Argentina [2]). Likewise, a high prevalence of seropositive dogs [4-6] and infected triatomines is routinely noted in rural and urban developments in southern US states [4, 7, 8] and suggested to maintain *T. cruzi* transmission in the human habitat. Triatomines are several times more likely to take their blood meal from dogs than from humans. The ratio of dog blood meals to human blood meals in the engorged guts of triatomines is estimated to be 2.3-2.6 times the ratio of the number of dogs to the number of humans in a household [9]. Thus, the probability of infecting an insect in one blood meal from dogs is estimated to be 200 times higher compared to the probability from adult humans [2]. These studies conclude: a) dogs are important host blood sources for domiciliary triatomines, b) the risk of *T. cruzi* infection in humans is increased by the presence of infected dogs, and c) strategies that can limit *T. cruzi* infection in the reservoir host would be effective in interrupting the parasite transmission to the vector, and consequently, to the human host.

The mathematical models based on epidemiological data suggest that vector control would be the most effective strategy against *T. cruzi* transmission [10]. However, sustained vector control, followed by constant surveillance, requires large-scale insecticide spraying every year that is not cost-effective and affordable for developing countries. Concerns also remain that insecticide use in the long-term may not be efficacious in blocking *T. cruzi* transmission, owing to the development of drug resistance by triatomines and reinfestation of homes by secondary sylvatic vectors, e.g., *Triatoma sordida*, in Brazil and other South American countries [11]. The same epidemiological models indicate that dog vaccination would be the second most efficient approach.

The efforts towards vaccine development are numerous. Based upon numerous studies in animal models, a successful vaccine that can provide protection from *T. cruzi* infection is envisioned by the research community to be composed of defined antigens capable of inducing strong neutralizing and lytic antibody response and type 1-biased T cell responses. Yet currently no vaccine is available for control of *T. cruzi* infection and disease development in humans and dogs.

Another major concern is the >300,000 infected individuals that have migrated to the US [25] (or other developed countries [26-27]) who can potentially transfer infection through blood or organ donation [28-29]. It is important that the migrant workforce in the US and the 20 million infected individuals living in the endemic countries [30] are diagnosed so as to prevent contamination of the donor blood banks. In the U.S., Ortho *T. Cruzi* ELISA Test System is licensed and approved by FDA for screening the donor blood samples. The Ortho System utilizes crude antigen preparation and there is a concern that crude antigen may exhibit cross-reactivity with antibodies to other parasitic protozoans (e.g. *Leishmania, Trypanosoma rangeli*) due to significant homology in the genome.

Thus, there is a recognized need in the art for a vaccine, a diagnosis composition and a treatment for control of *T. cruzi* infection and disease development in humans and dogs. The present invention fulfills this long-standing need and desire in the art.

SUMMARY OF THE INVENTION

The present invention is directed to a DNA vaccine comprising at least one plasmid encoding one or more GPI-anchored genes from *Trypanosoma cruzi*; at least one plasmid encoding a cytokine; and a pharmaceutically acceptable carrier.

The present invention is further directed to a DNA-protein vaccine comprising at least one plasmid encoding one or more GPI-anchored genes from *Trypanosoma cruzi*; at least one plasmid encoding a cytokine; one or more recombinant GPI-anchored proteins from *Trypanosoma cruzi*; and a pharmaceutically acceptable adjuvant.

The present invention is directed further to a vaccine comprising at least one plasmid encoding one or more GPI-anchored genes from *Trypanosoma cruzi*; at least one plasmid encoding a cytokine; one or more lysates comprising cells from *Trypanosoma rangeli* or other protozoa that are non-infective to humans; and a pharmaceutically acceptable adjuvant.

The present invention is directed still further to immunogenic proteins encoded by genes from *Trypanosoma cruzi*; one or more than one of these proteins comprise a composition along with a pharmaceutically acceptable carrier. This composition can be used in a method to detect *Trypanosoma cruzi* infection.

The present invention is directed further to antibodies specific for immunogenic proteins encoded by genes from *Trypanosoma cruzi*. These antibodies can be used in a method to detect or treat *Trypanosoma cruzi* infection.

The present invention is directed further to sense polynucleotide sequences and antisense polynucleotide sequences from *Trypanosoma cruzi*. These polynucleotide sequences can be used in a method to detect or treat *Trypanosoma cruzi* infection.

The present invention is directed further to a kit comprising one or more than one of the following components: immunogenic protein(s) from *Trypanosoma cruzi*, antibodies specific for immunogenic protein(s) encoded by gene(s) from *Trypanosoma cruzi*, sense polynucleotide sequence(s) and antisense polynucleotide sequence(s) from *Trypanosoma cruzi*, and a detection reagent.

Other and further objects, features, and advantages will be apparent from the following description of the presently preferred embodiments of the invention, which are given for the purpose of disclosure.

BRIEF DESCRIPTIONS OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 depicts the computational screening strategy used to screen the *T. cruzi* sequence database for the identification of potential vaccine candidates.

FIGS. 2A-2F depict expression plasmids used in the DNA vaccines. FIG. 2A depicts CMVI.UBF3/2 encoding ASP-2. The cDNA fragment of ASP-2 (GenBank accession no. U77951) encoding amino acid residues 61 to 705 (SEQ ID NO: 1) was cloned at BglII and SmaI restriction sites of multiple cloning sequence (MCS) in eukaryotic expression plasmid pCMV.UBF3/2CMVI.UBF3/2 mammalian expression plasmid containing the cytomegalovirus (CMV) immediate-early gene promoter, a Synthetic 5' intron, and a modified 3' untranslated region from the human growth hormone. The cloned genes were fused to a ubiquitin-encoding gene at the 5' end to promote targeting of the expressed protein to the proteosome and entry into the MHC class I pathway of antigen presentation. FIG. 2B shows pCDNA3 encoding TcG1-TcG8 cDNAs. The cDNA fragment of TcG1, TcG2, TcG3, TcG4, TcG5, TcG6, TcG7, and TcG8 were amplified using the oligonucleotides depicted in FIG. 2C, and cloned at indicated restriction sites in the eukaryotic expression plasmid pCDNA3.1. FIG. 2C depicts oligonucleotides used to amplify TcG1-TcG8 for cloning in pCDNA3. FIG. 2D depicts eukaryotic expression plasmids encoding murine granulocyte-macrophage colony-stimulating factor (GM-CSF; pCMVI.GM-CSF). FIG. 2E depicts eukaryotic expression plasmids encoding murine cytokine interleukin-12 (IL-12; pcDNA3.msp35 and pcDNA3.msp40). FIG. 2F depicts pCDNA3 encoding dog IL-12.

FIGS. 3A-3D depicts C57BL/6 mice immunized with pCDNA3 encoding TcG1, TcG2, and TcG4 plus IL-12 and GMCSF-expression plasmids (25 _g each plasmid/mouse, i.m., 3-week intervals) and then with recombinant protein cocktail (rTcG1, rTcG2, and rTcG4) with saponin adjuvant (25 _g each protein/mouse, i.d., 3-week intervals). Mice were challenged with *T. cruzi* 2-weeks after last immunization. FIG. 3A shows ab response after immunization and during acute (25 dpi) and chronic (>120 dpi) stages. FIGS. 3B-3C show Cytokine profile of splenocytes, in vitro activated with Tc lysate. FIG. 3D shows H&E staining, Controls+ were immunized with empty plasmid and saponin only (8 mice/group).

FIG. 4 depicts serological detection of anti-*T. cruzi* antibodies in vaccinated dogs. 96-well plates were coated with *T. cruzi* antigen ($5 \times 10^5$ parasite equivalents/well) or recombinant antigen (10 μg/well) and sequentially incubated with sera samples (1:20 dilution, 100 _l/well) added in triplicate; 100 _l/well HRP-labeled goat anti-dog IgG+M (1:5000 dilution) (KOMA); and 100 _l/well of Sure Blue TMB substrate (K&P). Absorbance was measured at 650 nm. Background signal (without serum) was subtracted before the data were calculated.

FIGS. 5A-5C depicts dogs (n=6) immunized with TcVac3$^R$ and two weeks later, challenged with *T. cruzi* (2300 parasites/kg). Control+ Dogs given empty vector/saponin only followed by challenge infection. FIG. 5A shows Parasitemia determined at 2-day intervals, beginning day 7 pi. FIG. 5B shows heart pathology, displaying ventricle fibrosis and atrial dilation in control$^+$ group. FIG. 5C shows that at 60 d post infection lab-reared triatomines were fed on vaccinated and control dogs (6 bugs/dog) Gut-parasitemia in triatomines was determined by light microscopic examination of diluted feces at 2 weeks-post feeding FIGS. 6A-6B depict that the TcG1, TcG2, and TcG4 genes are expressed in *T. cruzi*. FIG. 6A shows TcG1, TcG2, and TcG4 are expressed in epimastigote and amastigote stages and TcG1 and TcG4 are also expressed in trypomastigote stage of *T. cruzi*. RT-PCR was performed to evaluate mRNA levels for TcG1, TcG2 and TcG4 in different stages of *T. cruzi*. Total RNA and cDNA from the epimastigote (E), trypomastigote (T), and amastigote (A) forms of *T. cruzi* was obtained. FIG. 6B shows TcG1, TcG2, and TcG4 are phylogenetically conserved in CL Brenner (CL), Sylvio X10 (S), Brazil (Br), Y strain of *T. cruzi* (P: plasmid DNA used as control). Genomic DNA was isolated from different *T. cruzi* strains obtained from endemic countries. PCR amplified products were resolved by agarose gel electrophoresis, and imaged.

FIGS. 7A-7B depict that TcG1, TcG2, and TcG4 elicit antigen-specific antibody in mice. FIG. 7A shows the sera levels of parasite- and antigen-specific antibodies, measured two-weeks after the last immunization. FIG. 7B shows that TcG1, TcG2, and TcG4 are immunogenic in mice, and immune system of mice recognizes these proteins and elicit antigen-specific antibody response. Sera levels (1:100 dilution) of antibody response in normal mice (NM), and mice injected with pCNDA3 vector only (Vector), or cytokine (cyt) adjuvants only are shown as control. TcTL stands for total cell lysate of *T. cruzi*.

FIG. 8 shows sera level of antibodies in dogs immunized with candidate antigens (FIG. 8A) and infected with *T. cruzi* (FIG. 8B), measured by ELISA.

FIGS. 9A-9B depict that TcG1, TcG2 and TcG4 are equally or more effective in diagnosing the exposure to *T. cruzi*, compared to total cell lysate of *T. cruzi* (TcTL). Shown is a box plot of ELISA data, graphically depicting the OD values for seronegative (gray box) and seropositive (white box) samples from Mexico, identified by ELISA. (FIG. 9A): IgG response, (FIG. 9B): IgM response.

DETAILED DESCRIPTION OF THE INVENTION

Figure 1:

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); Sambrook, et al., Molecular Cloning: A Laboratory Manual (2nd Edition, 1989); Handbook of Surface and Colloidal Chemistry (Birdi, K. S. ed., CRC Press, 1997); Short Protocols in Molecular Biology, 4th ed. (Ausubel et al. eds., 1999, John Wiley & Sons); Molecular Biology Techniques: An Intensive Laboratory Course (Ream et al., eds., 1998, Academic Press); PCR (Introduction to Biotechniques Series), 2nd ed. (Newton & Graham eds., 1997, Springer Verlag); Peters and Dalrymple, Fields Virology, 2nd ed., Fields et al. (eds.) (B.N. Raven Press, New York, N.Y.).

As used herein the specification, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. Similarly, the word "or" is intended to include "and" unless the context clearly indicates otherwise. "Comprise" means "include." It is further to be understood that all base sizes or amino acid sizes, and all molecular weight or molecular mass values, given for nucleic acids or polypeptides are approximate, and are provided for description. Although methods and materials similar or equivalents to those described herein can be used in the practice or testing of the present disclosure, suitable methods and materials are described below. In case of conflict, the present specification, including explanations of terms, will control. In addition, the materials, methods, and examples are illustrative only and not intended to be limiting. Furthermore, unless otherwise required by context, singular terms shall include pluralities and plural terms shall include the singular.

The term "antigen" as used herein is defined as a compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance.

An "antigen" can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a prostate specific antigen. A disease-specific antigen is expressed coincidentally with a disease process. Specific non-limiting examples of a disease-specific antigen are an antigen whose expression correlates with, or is predictive of, tumor formation, such as prostate cancer. A disease specific antigen may be an antigen recognized by T cells or B cells.

The term "amplification" of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

The term "antibody" as used herein includes immunoglobulin molecules and immunologically active portions of immunoglobulin molecules, i.e., molecules that contain an antigen binding site that specifically binds (immunoreacts with) an antigen. A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al., Nature 341:544-546, 1989) which consists of a $V_H$ domain; (v) an isolated complimentarily determining region (CDR); and (vi) a $F(ab')_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faoulkner et al., Nature 298:286, 1982; Morrison, J. Immunol. 123:793, 1979; Morrison et al., Ann Rev. Immunol 2:239, 1984).

The term "animal" as used herein refers to living multi-cellular vertebrate organisms, a category that includes, for example, mammals and birds. The term mammal includes both human and non-human mammals. Similarly, the term "subject" includes both human and veterinary subjects.

The term conservative variation includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity.

The term "cDNA" (complementary DNA) refers to a piece of DNA lacking internal, non-coding segments (introns) and regulatory sequences that determine transcription. cDNA is synthesized in the laboratory by reverse transcription from messenger RNA extracted from cells.

The term "diagnostic" refers to identifying the presence or nature of a pathologic condition, such as, but not limited to, prostate cancer. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathological condition, such as prostate cancer, or metastasis.

An "epitope" as used herein, is an antigenic determinant. These are particular chemical groups or peptide sequences on a molecule that are antigenic, i.e. that elicit a specific immune response. An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "expression control sequence" refers to Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e. ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

The term "promoter" refers to a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., Methods in Enzymology 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

As defined herein, the term "host cell" refers to cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

The term "immune response" refers to a response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

An "isolated" biological component (such as a nucleic acid or protein or organelle) as defined herein, has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

A "label" as defined herein, is a detectable compound or composition that is conjugated directly or indirectly to another molecule to facilitate detection of that molecule. Specific, non-limiting examples of labels include fluorescent tags, enzymatic linkages, and radioactive isotopes.

Lymphocytes as defined herein are a type of white blood cell that is involved in the immune defenses of the body. There are two main types of lymphocytes: B cells and T cells.

Open reading frame (ORF) is defined as a series of nucleotide triplets (codons) coding for amino acids without any internal termination codons. These sequences are usually translatable into a peptide.

The term "operably linked" refers to a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

As used herein, the term "vector" refers to a nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

As used herein, the term "transduction" encompasses all techniques by which a nucleic acid molecule might be introduced into such a cell, including transfection with viral vectors, transformation with plasmid vectors, and introduction of naked DNA by electroporation, lipofection, and particle gun acceleration. A transduced cell is a cell into which has been introduced a nucleic acid molecule by molecular biology techniques.

As used herein, the term "T Cell" refers to a white blood cell critical to the immune response. T cells include, but are not limited to, CD4+ T cells and CD8+ T cells. A CD4+ T lymphocyte is an immune cell that carries a marker on its surface known as "cluster of differentiation 4" (CD4). These cells, also known as helper T cells, help orchestrate the immune response, including antibody responses as well as killer T cell responses. CD8+ T cells carry the "cluster of differentiation 8" (CD8) marker. In one embodiment, a CD8 T cell is a cytotoxic T lymphocyte. In another embodiment, a CD8 cell is a suppressor T cell.

The term "purified" as used herein, does not require absolute purity; rather, it is intended as a relative term. Thus, for example, a purified nucleic acid is one in which the nucleic acid is more enriched than the nucleic acid in its natural environment within a cell. Similarly, a purified peptide preparation is one in which the peptide or protein is more enriched than the peptide or protein is in its natural environment within a cell. In one embodiment, a preparation is purified such that the protein or peptide represents at least 50% (such as, but not limited to, 70%, 80%, 90%, 95%, 98% or 99%) of the total peptide or protein content of the preparation.

A "recombinant nucleic acid" is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

As used herein, the term "selectively hybridize" refers to hybridization under moderately or highly stringent conditions that excludes non-related nucleotide sequences. In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA versus DNA) of the hybridizing regions of the nucleic acids can be considered in selecting hybridization conditions. An additional consideration is whether one of the nucleic acids is immobilized, for example, on a filter. One of skill in the art can readily determine these conditions (e.g., Molecular Cloning: A Laboratory Manual, 2nd ed., vol. 1-3, ed. Sambrook et al., Cold Spring Harbor Laboratory Press, Cold Spring Harbor, N.Y., 1989). As mentioned above, optimal conditions will vary, depending on the particular hybridization reaction involved, and can be determined empirically.

The term "polynucleotide" or "nucleic acid sequence" refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

The term peptide, as used herein refers to any chain of amino acids, regardless of length or post-translational modification (e.g., glycosylation or phosphorylation).

The term "probe" comprises an isolated nucleic acid attached to a detectable label or reporter molecule. The term "primer" includes short nucleic acids, preferably DNA oligonucleotides, 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

The term "promoter" as described herein, is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g., Bitter et al., Methods in Enzymology 153:516-544, 1987). Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

The pharmaceutically acceptable carriers of use are conventional. Remington's Pharmaceutical Sciences, by E. W. Martin, Mack Publishing Co., Easton, Pa., 15th Edition (1975), describes compositions and formulations suitable for pharmaceutical delivery of the vaccines herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the term "subject" refers to any target of the treatment. Preferably, the subject is a mammal, more preferably, the subject is a canine or a human.

In some embodiments of the present invention there is provided a DNA vaccine comprising at least one plasmid encoding one or more GPI-anchored genes from *Trypanosoma cruzi*; at least one plasmid encoding a cytokine; and a pharmaceutically acceptable carrier.

Further to these embodiments, representative GPI-anchored genes are ASP-2, TcG-1, TcG2, TcG3, TcG4, TcG5, TcG6, TcG7 and TcG8. These GPI-anchored genes encode proteins with sequences shown in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. Additionally, in some embodiments, representative cytokines are selected from the group comprising IL12, GM-CSF, CD40L, Flt3L and RANTES. In some embodiments, GPI-anchored genes are selected from ASP-2 encoding a protein with a sequence shown in SEQ ID NO: 1, TcG-1 encoding a protein with a sequence shown in SEQ ID NO: 2, TcG-2 encoding a protein with a sequence shown in SEQ ID NO: 3, and TcG4 encoding a protein with a sequence shown in SEQ ID NO: 5; and the cytokines are IL-12 and GM-CSF. In some embodiments, the DNA vaccine comprises 100 µg of each plasmid.

In some embodiments of the present invention, there is provided a DNA-protein vaccine comprising at least one plasmid encoding one or more GPI-anchored genes from *Trypanosoma cruzi*; at least one plasmid encoding a cytokine; one or more recombinant GPI-anchored proteins from *Trypanosoma cruzi*; and a pharmaceutically acceptable adjuvant. In some of these embodiments, representative GPI-anchored genes include but are not limited to ASP-2, TcG-1, TcG2, TcG3, TcG4, TcG5, TcG6, TcG7 and TcG8. These GPI-anchored genes encode proteins with sequences shown in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. Further to these embodiments, representative recombinant GPI-anchored proteins may be ASP-2, TcG-1, TcG2, TcG3, TcG4, TcG5, TcG6, TcG7 and TcG8. In some of these embodiments, recombinant GPI-anchored proteins have sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. In some embodiments, the adjuvant is a saponin adjuvant.

In another embodiment of the present invention, there is provided a vaccine comprising at least one plasmid encoding one or more GPI-anchored genes from *Trypanosoma cruzi*; at least one plasmid encoding a cytokine; one or more lysates comprising cells from *Trypanosoma rangeli* or other protozoa that are non-infective to humans; and a pharmaceutically acceptable adjuvant.

Certain embodiments of the invention comprise methods of vaccination comprising one or more of the vaccines described supra. In certain embodiments, these methods are used in vaccinating dogs. In certain embodiments, the vaccines comprise from about 50 µg to about 500 µg of each plasmid. In other embodiments, the vaccines may comprise from about 50 µg to about 500 µg of each recombinant GPI-anchored protein. In certain embodiments, the vaccines comprise from about 50 µg up to about 900 µg of the bacterial cell lysates comprising *Trypanosoma rangeli* cells.

In yet another embodiment of the present invention, there is provided an isolated protein or protein fragment with at least 90% sequence identity to a protein having the sequence shown in SEQ ID NO: 2 encoded by a TcG-1 gene *Trypanosoma cruzi*; or a protein with a sequence shown in SEQ ID NO: 3 encoded by a TcG-2 gene *Trypanosoma cruzi*; or a protein with a sequence shown in SEQ ID NO: 5 encoded by a TcG-4 gene of *Trypanosoma cruzi*. Further to these embodiments, the protein or protein fragment is a synthetic or a recombinant protein or protein fragment.

In yet another embodiment of the present invention, there is provided an immunogenic composition, comprising one or more of the isolated protein or protein fragment of the TcG-1, TcG-2 or TcG-4 proteins and a pharmaceutically acceptable carrier. Further to these embodiments, immunogenic composition exhibits reactivity with sera from a subject infected with *Trypanosoma cruzi*.

In yet another embodiment of the present invention, there is provided an isolated or purified antibody or antibody fragment thereof that specifically binds the protein or protein fragment of the TcG-1, TcG-2 or TcG-4 protein. In yet another embodiment of the present invention, there is provided a synthetic polynucleotide sequence encoding the protein or protein fragment of the TcG-1, TcG-2 or TcG-4 protein. In yet another embodiment of the present invention, there is provided a synthetic antisense polynucleotide sequence that is complementary to at least part of the synthetic polynucleotide sequence that encodes the TcG-1, TcG-2 or TcG-4 protein.

In yet another embodiment of the present invention, there is provided a method for detecting *Trypanosoma cruzi* infection in subject. This method comprising the steps of: contacting a sample isolated from a subject with the composition comprising one or more than one of the TcG-1, TcG-2 or TcG-4 proteins; detecting the specific antibody response from the isolated sample to said composition, wherein an increase of the antibody response indicates that the subject is infected with *Trypanosoma cruzi*. Representative antibody responses include but are not limited to an IgG antibody response and an IgM antibody response. Representative isolated samples include but are not limited to serum or blood.

Further to these embodiments, the isolated sample is contacted with: a protein with a sequence shown in SEQ ID NO: 2 encoded by a TcG-1 gene *Trypanosoma cruzi*; a protein with a sequence shown in SEQ ID NO: 3 encoded by a TcG-2 gene *Trypanosoma cruzi*; and a protein with a sequence shown in SEQ ID NO: 5 encoded by a TcG-4 gene of *Trypanosoma cruzi*, wherein an increase of the antibody responses in said isolated sample to all three antigens indicates that the subject is infected with *Trypanosoma cruzi*.

In yet another embodiment of the present invention, there is provided a method for detecting *Trypanosoma cruzi* infection in a subject, said method comprising the steps of: labeling an antibody or antibody fragment that binds the TcG-1, TcG-2 or TcG-4 protein, with a detectable substrate; contacting a sample isolated from a subject with the labeled antibody or antibody fragment; detecting the binding of the labeled antibody or antibody fragment to the sample, wherein an increase of binding of the labeled antibody to the isolated sample indicates that the subject is infected with *Trypanosoma cruzi*.

In yet another embodiment of the present invention, there is provided a method for detecting *Trypanosoma cruzi* infection in a subject, said method comprising the steps of: generating an antisense polynucleotide sequence that is complementary to at least part of the polynucleotide sequence encoding the protein or protein fragment of the TcG-1, TcG-2 or TcG-4 protein; labeling the antisense polynucleotide with a detectable substrate, isolating nucleic acids from a sample from a subject; amplifying the polynucleotide sequence encoding the protein or protein fragment of the TcG-1, TcG-2 or TcG-4 protein from the nucleic acids; contacting the amplified polynucleotide sequence with labeled antisense polynucleotide, wherein an increase of binding of the labeled antisense polynucleotide to the amplified polynucleotide sequence indicates that said subjected is infected with *Trypanosoma cruzi*.

In yet another embodiment of the present invention, there is provided a method for treating *Trypanosoma cruzi* infection in subject, said method comprising the step of: administering the antibody or antibody fragment that binds the TcG-1, TcG-2 or TcG-4 protein to a subject infected with *Trypanosoma cruzi*, so as to decrease amount of *Trypanosoma cruzi* in the subject thereby treating the *Trypanosoma cruzi* infection.

In yet another embodiment of the present invention, there is provided a method for treating *Trypanosoma cruzi* infection in a subject, said method comprising the step of: administering the synthetic antisense polynucleotide sequence that encodes the TcG-1, TcG-2 or TcG-4 protein to a subject infected with *Trypanosoma cruzi*, so as to decrease *Trypanosoma cruzi* in the subject thereby treating the *Trypanosoma cruzi* infection.

In yet another embodiment of the present invention, there is provided a kit for detecting *Trypanosoma cruzi* infection in a sample, said kit comprising: (a) one or more of the isolated protein or protein fragment of the TcG-1, TcG-2 or TcG-4 protein; and (b) a detection reagent. Further to this embodiments, the kit contains: a protein with a sequence shown in SEQ ID NO: 2 encoded by a TcG-1 gene *Trypanosoma cruzi*; a protein with a sequence shown in SEQ ID NO: 3 encoded by a TcG-2 gene *Trypanosoma cruzi*; a protein with a sequence shown in SEQ ID NO: 5 encoded by a TcG-4 gene of *Trypanosoma cruzi*; and a detection reagent.

In yet another embodiment of the present invention, there is provided a kit for detecting *Trypanosoma cruzi* infection in a biological sample, said kit comprising: (a) one or more isolated or synthetic antibody or antibody fragment that specifically binds the protein or protein fragment of the TcG-1, TcG-2 or TcG-4 protein; and (b) a detection reagent. In this embodiment of the present invention, there is provided a kit for detecting *Trypanosoma cruzi* infection a biological sample, said kit comprising: (a) one or more of the isolated protein or protein fragment of the TcG-1, TcG-2 or TcG-4 protein; and (b) one or more isolated or synthetic antibody or antibody fragment that specifically binds the protein or protein fragment of the TcG-1, TcG-2 or TcG-4 protein; and (c) a detection reagent.

In yet another embodiment of the present invention, there is provided a kit for detecting *Trypanosoma cruzi* infection a biological sample, said kit comprising: (a) one or more of the synthetic antisense polynucleotide sequence that encodes the TcG-1, TcG-2 or TcG-4 protein; and (b) a detection reagent.

The following examples are given for the purpose of illustrating various embodiments of the invention and are not meant to limit the present invention in any fashion.

Example 1

Vaccine Development

A transfection approach is employed to express ovalbumin (model antigen) in different cellular compartments of *T. cruzi*. Using these transfectants, it has been demonstrated that parasite secreted antigens and GPI-proteins (released by default in host cell cytoplasm) would be capable of entering the class I and II pathways of antigen presentation and elicit antibody and T cell responses, and, thus, would be the best choice as vaccine candidates [12].

Example 2

Computational Screening

An unbiased computational/bioinformatics approach was developed and the *T. cruzi* sequence database was screened for the identification of potential vaccine candidates [18] (FIG. 1). This strategy was chosen because testing of ~8,000 genes, estimated to be present in the haploid genome of *T. cruzi* (5-8×$10^7$ bp), as subunit vaccine candidates was not economically feasible. Strategic analysis of the database led to a selection of 71 candidate sequences of which eight (TcG1-TcG8, Table 1: SEQ ID NOs 2-9) were found to be phylogenetically conserved in clinically important strains of *T. cruzi*, and expressed in the infective and intracellular stages of the parasite [18]. When delivered as a DNA vaccine in mice, TcG1, TcG2, TcG4 elicited a significant trypanolytic antibody response and Th1 cytokine (IFN-γ), a property associated with immune control of *T. cruzi [*18] (Table 2). These vaccine candidates, thus, increased the pool of protective vaccine candidates against *T. cruzi*.

Example 3

Protective Efficacy of TcG1, TcG2, and TcG4 in Mice

TcG1, TcG2, and TcG4 were cloned in eukaryotic expression vector pCDNA3.1 (for DNA vaccination) and in *E. coli* expression vector to generate recombinant proteins (for protein vaccination). One group of mice was immunized with four doses of DNA vaccine (pcDNA3 encoding TcG1, TcG2, and TcG4+ IL-12 and GM-CSF expression plasmids as illustrated in FIGS. 2A-2F, intramuscular delivery). Second group of mice was immunized with 2 doses of DNA vaccine and 2 doses of recombinant proteins with saponin adjuvant (intradermal). Both groups of mice immunized with DNA-DNA or DNA-protein vaccine elicited anti-parasite humoral and cellular immune responses (FIGS. 3A-3D) [19].

The DNA-protein vaccine of the present invention induced significantly higher levels of *T. cruzi*- and antigen-specific humoral responses that were maintained after challenge infection and during chronic disease phase. Likewise, the DNA-protein vaccine elicited a stronger, Th1 biased cellular response (IFN-_, TNF-_ cytokines, $CD8^+$T cells) that was effective in controlling the acute parasitemia and tissue parasite burden during acute phase. Due to controlled acute infection, DNA-protein vaccinated mice exhibited remarkable reduction in immunopathology, a hallmark of chronic Chagas disease. Overall DNA-protein vaccine polarized the B & T cell immune response towards Th1 type that controlled parasites during acute phase and towards Th2 type after acute infection that reduced chronic inflammation during disease phase, respectively. These studies suggested that DNA/protein vaccination would be a better approach in eliciting protective immunity against *T. cruzi* infection and disease.

TABLE 1

Genes phylogenetically conserved in clinically important strains of *T. cruzi*.

| Gene | SEQ ID | SEQUENCE |
|---|---|---|
| ASP-2 | SEQ ID NO: 1 | PCEAADAVEGKSGAVQLPKWVDIFVPEKTHVLPKEGSESGVKKAFA<br>APSLVSAGGVMVAFAEGFSEYNAHENNPFGIRPYEILAGYIKAAESW<br>PSIVAEVNASTWRAHTVIGSRNGNDRLCFLYRPTAVARENKVFLLVG<br>SDTVGYDSDDDMWVKDGWDIQLVEGVATQSTDGKPSKTINWGEPK<br>SLLKHIPKHTQGHLRDVVTAGGSGIVMQNNTLVFPLVVNGKNYPFSS<br>ITYSTDNGNNWVFPESISPVGCLDPRITEWETGQILMIVDCGNGQSV<br>YESRDMGTTWTKAVRTLSGVWAISQRGVRSYEIFRVGAIITATIEGR<br>KVMLYTRRGYASGEKEANALYLWVTDNNRTFHVGPVAMDSAVNET<br>LSNALLYSDGNLHLLQQRANEKGSAISLARLTEELKEIESVLRTWAQL<br>DAFFSKSSTPTAGLVGFLSNTSSGGNTWIDEYRCVNATVTKASKVK<br>NGFKFTGPGPMATWLVNSREDNRQYSFVNHRFTLVATVTIHQVPKG<br>STPLLGAGLGDGHGAKIIGLSYSMNKTWETVFYGKKTTSNTTWELG<br>KEYQVTLMLQDGNKGSVYVDGVIVGSPAKIPKVGALGHEIAHFYFGG<br>GEGDSDSSVTVTNVFLYNRPLSVGELKMVRKSDDKKGNGGDQK |
| TcG1 | SEQ ID NO: 2 | MVKANYIRAGRLVRIIRGPRQDRVGVVVDIIDGNRVLVENPADKKMW<br>RHVQNLKNVEPLKFSVELSRNCSTRTLKNVLAEKKILEKYAATKSAR<br>RIAAKRAFARSTDFERYQLRVAKRSRAFWTRKVFDENDQKKPVSW<br>HKVALKKLQKNAKKVDSKPAAKKRISN |
| TcG2 | SEQ ID NO: 3 | MSLSFIESGFVPSDGMRRGVEAADTSAAAELLHLAVPPLMDAGGKT<br>RVCVAFYEAAQCPFDSRCEHAHHFSELNGYTQNKLLETVPVESIPK<br>HFVAPLNSNSSSGNNKNDRTFYATDGNAANYTATAAVDGGVAHRS<br>LGGEHGEKEKTSTNRRSKRTARLYDISGSNTNLCDNSLSSLASSTDT<br>LLLLGSVHDSKDVSPQKGTRRDEGMEAFRIRLPPLLG |
| TcG3 | SEQ ID NO: 4 | MLQRTCSGSLYAVLEVARDATPQEIKKAYHRLALRLHPDKTGGTTTE<br>QFTLIQEAQSILGDPRQRRVYDTFGRMGIESLRQFGDGMVVMTTAGI<br>RCAFFIIAFWMLLWLLTLVLAIVRFDYNKGWPWAAVFAPVWVALVPL<br>LLIGGLLVFHGATRREIASTLLGLMCFLVTFAVAMFVVGLSGALTWTI<br>ALAPSAAIYVFQSCFILRYLLPFQFRNGFAEFIPPGSSVCLSRMYWGF<br>CWKQYLKSCVVSALLVLPCYRGANRRGRYIKTDLLLDSFYSSYFVL<br>WVHDVCFCRTKIFCGNSGGAVMSPEPTVPCADGRHRLRQSSFYGM<br>HVGGEVSS |
| TcG4 | SEQ ID NO: 5 | MSAKAPPKTLHQVRNVAYIFAAWAGLQKGFAEKSANDKMWVEHQR<br>RLRQENAKRQHAAHALEELKQDEELERSIPTIVPKELHELVKALEK |
| TcG5 | SEQ ID NO: 6 | MGKEKVHMNLVVVGHVDAGKSTATGHLIYKCGGIDKRTIEKFEKEA<br>AEIGKSSFKYAWVLDKLKAERERGITIDIALWKFESPKSVFTIIDAPG<br>HRDFIKNMITGTSQADAAVLVIASSQGEFEAGISKDGQTREHALLAF<br>TLGVKQMVVCCNKMDDKSVNFAQERYDEIVKEVSAYLKKVGYNVE<br>KVRFIPISGWQGDNMIDKSENMPWYKGPTLLEALDMLEPPVRPSD<br>KPLRLPLQDVYKIGGIGTVPVGRVETGTMKPGDVVTFAPANVTTEV<br>KSIEMHHEQLAEATPGDNVGFNVKNVSVKDIRRGNVCGNSKNDPP<br>KEAADFTAQVIILNHPGQIGNGYAPVLDCHTCHIACKFAEIESKIDRR<br>SGKELEKNPKSIKSGDAAMVRMVPQKPMCVEVFNDYAPLGRFAVR<br>DMRQTVAVGIIKAVTKKDGGAGKVTKAAAKAAKK |
| TcG6 | SEQ ID NO: 7 | MQSELSGILSRIPAAVIGTILADESCKTVWFFNPKSREVISMDALRSL<br>PNPPSNSGADATERHLVYGMMRVRNQGVMFERDHIQRLYENCVL<br>AATSKPLTDEATLPFPVEGVTQSIREYILSEHKESGDINLKFVTWLPP<br>FSNSLTTAEAWQKFLSDFSYVVYFVKSFFPPKEWYTEGIRISLLYNA<br>RRHTPNAKIIQAPLRSRAKSLQDSSGAFEVFFVWDKEAHFLVPEGS<br>RSNYLLVTEDGHLCCSLAV |
| TcG7 | SEQ ID NO: 8 | MLATHGRGRRVQGAVGAVFSFEEGKRGKTRRAPLTSQNARKKKT<br>VKSIAASCGADPDILHERNSTALLKEGDGVVYSAVPKYKQSRLGVL<br>LQHPLYSPHVVCCRFVCCVRLRRGWM |
| TcG8 | SEQ ID NO: 9 | MSDNHQLEYKRGLEDARRHRSRTEDNWLRASVGPLLWFGVPFAV<br>AWLYLRRQAPASAKINPFGGMMEQMMPIKKRQFRVDVKGTKFEDV<br>IGIPEAKQEVQQYVEFLTNPNKFTRLGARLPKGRLLTGEPGTGKTLL<br>AKAVAGEADVPFFSCSGSDFIELMGGSGPKRVRELFEEARSSAPAI<br>VFIDEIDAIGSRAGKIGGSVSSEENRTINQLLAELDGLNTGTDAIIVIA<br>ATNFQDNIDKALLREGRFDRKVNIEMPDKAARVDIFKHYLNRVGTG<br>DPRGRKVDEEGEPLPTNEKVDNLELARELADLTPGVSPATIATIVNE<br>AALQSGIREKRLVDKESILEAVDNTLVGRKHRNRQSVTSLRRTAIHE<br>AGHALTAWMLPSVKQVLKVSVVPQ |

TABLE 2

Screening immunogenic potential of antigens as DNA vaccine in mice.

| Immunization with | Mice | Elicitation of immune response by vaccine | | | Pathological parameters after challenge infection* | |
|---|---|---|---|---|---|---|
| | | Antibodies (IgG + M) | CTL activity | Th1 cytokine IFNγ, IL-12 | Control of Inflammation | Percent Survival[a-c] |
| None | | − | − | − | − | 10[c] |
| ASP-1 | C3H/HeSnJ, C57BL/6 | +/− | + | + | + | 40[b] |
| TSA-1 | Balb/c, C3H/He, C57B/6 | +/− | + | + | + | 30[b] |
| ASP-2 | C3H/HeSnJ, C57BL/6 | + | ++ | ++ | ++ | 62[b] |
| ASP-1 + ASP-2 + TSA-1 | C3H/HeSnJ, C57BL/6 | + | ++ | ++ | ++ | 68[a] |
| ASP-2 + IL-12 + GM-CSF[d] | C3H/HeSnJ, C57BL/6 | ++ | +++ | + | +++ | 80[a] |
| TcG1 + IL-12 + GM-CSF[d] | C57BL/6 | ++ | ND | + | ++ | 90[b] |
| TcG2 + IL-12 + GMCSF[d] | C57BL/6 | ++ | ND | + | ++ | 92[b] |
| TcG4 + IL-12 + GMCSF[d] | C57BL/6 | ++ | ND | + | +++ | 100[b] |
| ASP-1 + ASP-2 + TSA-1 + IL-12 + GM-CSF[d] | C3H/HeSnJ, C57BL/6 | +++ | +++ | ++ | +++ | 83[a] |

Mice were intra-muscularly immunized with antigen-encoding plasmids ± cytokine expression constructs (33 μg each DNA/mouse) twice at six-week intervals. Two week after 2$^{nd}$ immunization, mice were either used for measuring immune responses, or challenged with *T. cruzi*.
*Immunization protocol provided variable degree of protection in different mouse strains.
$^{a-c}$Upon challenge infection, immunized animals exhibited very low (≤10%)$^a$, moderate (~50%)$^b$ or similar$^c$ parasitemia as detected in un-immunized/infected animals (data presented are from the animal model that exhibited best protection).
$^d$Immunization with these antigens was effective in decreasing the severity of chronic disease, evaluated by histopathological analysis of cardiac tissue biopsies..
A "+" or "−" sign indicates the effectiveness or limitation of the genetic vaccine in eliciting immune responses and protection from *T. cruzi* infection, respectively.
ND: not determined.

Example 4

Immunogenicity of Vaccine Candidates in Dogs

The protective efficacy of selected vaccine candidates in dogs was determined. The candidate antigens included in dog studies were those that have exhibited maximal protection in murine studies.
TcVac1$^R$ Vaccine
pCDNA3 encoding TcG1, TcG2 and TcG4+ IL-12 and GM-CSF expression plasmids. 100 μg each plasmid, total 600 μg DNA. Four doses, intramuscular delivery, 2-week intervals.
TcVac2$^R$ Vaccine
Two doses of TcVac1$^R$ followed by two doses of recombinant proteins (TcG1, TcG2, TcG4 with saponin adjuvant (DNA vaccine: im, 600-μg total DNA/dog; protein vaccine: id, 300 μg protein/dog, all doses at 2-week intervals). The recombinant proteins (TcG1, TcG2, and TcG4) were prepared in *E. coli*. No other study has demonstrated the protection afforded by this cocktail of antigens against *T. cruzi* in any model of disease.

Example 5

Antibody Response

Figure 4:
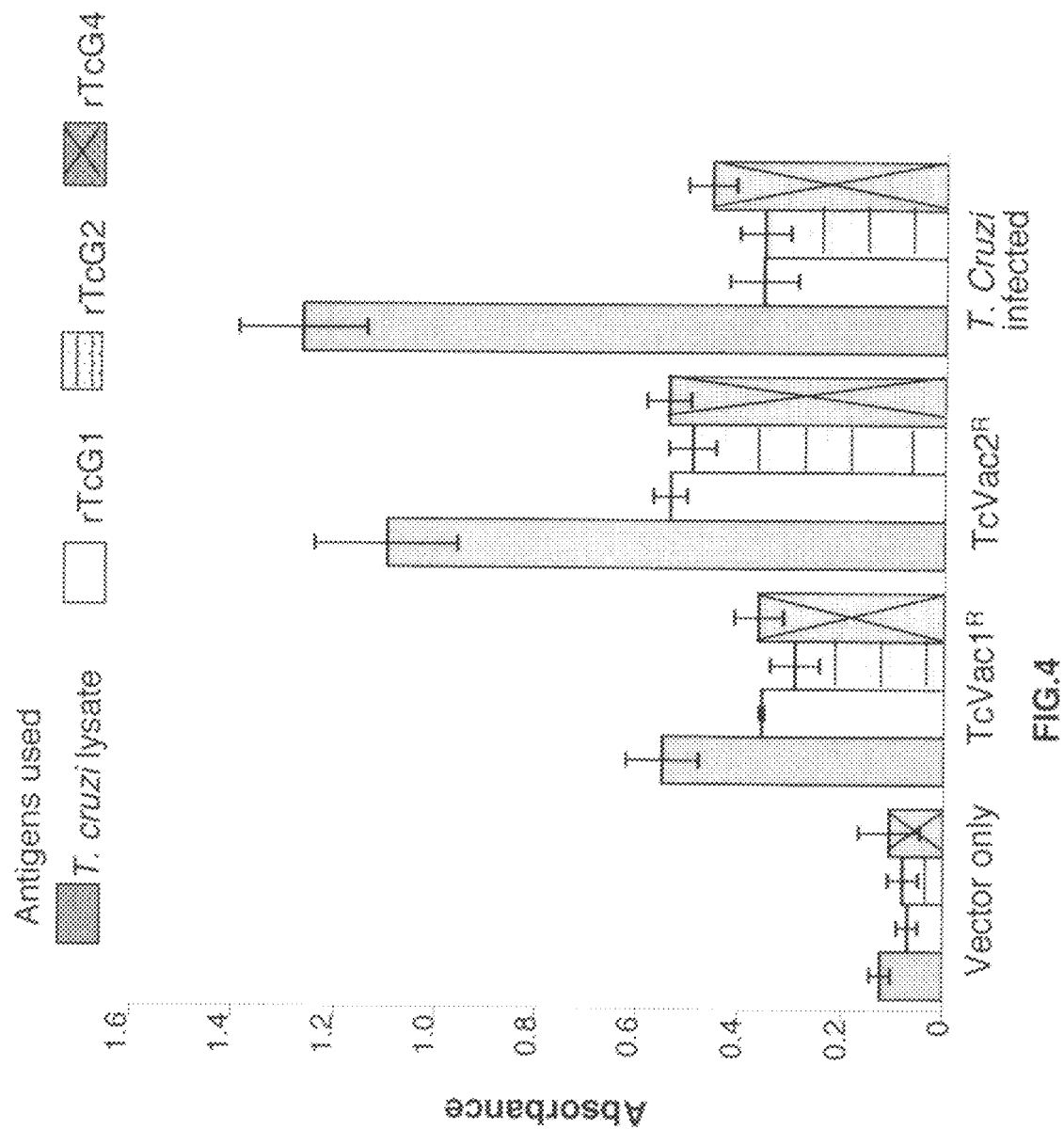

*T. cruzi* and antigen-specific antibody response were determined in sera obtained from vaccinated dogs before each immunization, and 2 weeks after the last immunization. Negative control: sera from dogs immunized with vector only. Positive control: Sera from *T. cruzi*-infected dogs. It was found that after a second dose of DNA vaccine, antigen-specific antibody responses were elicited and these were enhanced by booster immunization with recombinant protein doses of TcVac2$^R$. An antibody response to individual candidate genes was elicited in vaccinated dogs, and it was similar to that detected in chronically infected dogs. Shown in FIG. 4 are the parasite- and recombinant antigen-specific antibody response in sera collected after the last immunization.

Example 6

Trypanolytic Activity

Trypanolytic activity correlates with protection from *T. cruzi* infection as antibodies to surface proteins (plus complement) induce damage to infective trypomastigotes [20, 21]. Trypanocidal activity of the antibodies elicited was determined in dogs vaccinated with TcVac1$^R$ using procedures standardized in the lab [18]. The sera from vaccinated dogs, obtained after 4$^{th}$ immunization, provided ≥80% lytic efficiency (1:8 dilution). In comparison, sera from *T. cruzi*-infected dogs exposed to multiple parasite proteins exhibited 90% lytic activity. No parasite lysis was observed with negative control sera from dogs immunized with empty vector, or when heat-inactivated immune sera or heat-inactivated complement were used. Together, these data show that dogs immunized with TcVac1$^R$ elicit antigen-specific antibody responses that are trypanolytic in nature, and hence capable of providing protection from *T. cruzi* infection.

TABLE 3

| Trypanolytic activity of antisera from vaccinated dogs | % lytic activity Sera dilution | | |
|---|---|---|---|
| Antiserum from dogs immunized with | 1:4 | 1:8 | 1:16 |
| Vector only | 0 | 0 | 0 |
| TcVac2$^R$ | 90 | 81 | 62 |
| *T. cruzi*-infected | 100 | 92 | 81 |

Chronic serum was obtained from lab-infected dogs. Immune sera from vaccinated dogs were obtained after 4$^{th}$ immunization (as for FIG. 3). *T. cruzi* trypomastigotes ($5 \times 10^4$/25 µl were incubated for 4 h at 37° C., 5% $CO_2$ with 25 µl two-fold dilution of sera samples + 25 µl/well human complement (Sigma). The live, freely moving parasites were counted by light microscopy. Parasites that stained positively with 0.03% trypan blue were considered dead. All samples were analyzed in triplicate.
Percent trypanocidal efficiency: (Total parasites − free parasites after incubation/Total parasites) × 100
SD was ≤10%, n = 3/gp.

Example 7

TcVac3$^R$ Vaccine

Protective and Transmission Blocking Efficacy

To simplify vaccine composition and reduce the cost of production, TcVac3$^R$ was designed in which recombinant proteins were replaced by equivalent amount of protein lysate of *T. rangeli* (non-pathogenic in mammals and humans).
TcVac3$^R$ Vaccine Two doses of DNA vaccine containing four expression plasmids+cytokine expression plasmids followed by two doses of *T. rangeli* lysates with saponin adjuvant (n=6, DNA vaccine: im, 600-µg DNA/dog; *T. rangeli* lysate: id, 400 µg protein/dog, all doses at 3-week intervals). Vaccinated dogs exhibited up to 8-fold decline in acute parasitemia (FIG. 5A), and a significant decline in myocardial pathology evidenced by decreased fibrosis in left ventricle and decreased dilation of right ventricle (FIG. 5B) when compared to controls that were immunized with empty vector only and infected with *T. cruzi*. Clinical exam (EKG analysis) of TcVac3$^R$ vaccinated dogs detected no alterations while control+ dogs exhibited symptoms of conduction problems, myocarditis and/or pericarditis (Table 4).

TABLE 4

| Echocardiographic findings | | | |
|---|---|---|---|
| TcVac1$^R$ | TcVac3$^R$ | CONTROL+ | CONTROL− |
| 1.-Ventricular dilatation | 1.-No alterations | 1.-Repolarization problems myocarditis | 1.-No alterations |
| 2.-Repolarization problems myocarditis | 2.-No alterations | 2.-Myocarditis | 2.-No alterations |
| 3.-No alterations | 3.-No alterations | 3.-Pericarditis | 3.-No alterations |

In the above experiments, the infectivity of the dogs to triatomines was determined by feeding the insects on abdomen skin using a membrane-feeding apparatus. Importantly, xenodiagnostic studies (FIG. 5C) showed that >88% of bugs (23/26) fed on control+ dogs were infected while only 50% bugs (15/30) bugs fed on TcVac$^R$ vaccinated dogs became infected, thus demonstrating at least 50% reduction in infectivity (Table 5).

TABLE 5

| Transmission blocking efficiency. | | |
|---|---|---|
| Groups | # infected/Total bugs fed on dogs | % Infectivity |
| TcVac1$^R$ | 10/19 | 52.63 |
| TcVac3$^R$ | 15/30 | 50 |
| CONTROL+ | 23/26 | 88.46 |
| CONTROL− | 0 | 0 |

Triatomines (6 per dog) were fed on vaccinated or control dogs (6 dogs per group) at day 60 pi. The infectivity of triatomines was determined by light microscopic examination for metacyclic trypomastigotes in diluted feces of bugs.

Example 8

Utilizing TcG1, TcG2, and TcG4 for Screening Sero-Prevalence and Diagnosis of Exposure to *T. cruzi*

Three proteins, encoded respectively by TcG1, TcG2 and TcG4, are proposed herein for the diagnosis of exposure to *T. cruzi* infection. These proteins serve as diagnostic markers, are useful in screening blood banks, evaluating seroprevalence in humans, and animal population in domestic or non-domestic environments. An ELISA kit containing the three antigens together or a dip-stick coated with the three antigens together will provide >98% sensitivity and >98% specificity for diagnosis of exposure to *T. cruzi.*

Example 9

TcG1, TcG2, TcG4 are Expressed in Infective Stage of *T. cruzi*

To establish the diagnostic utility of TcG1, TcG2, and TcG4, it is important that these genes are expressed in infective stage of *T. cruzi* and expressed in diverse strains of *T. cruzi*. For this, RT-PCR was performed to evaluate mRNA levels for TcG1, TcG2 and TcG4 (along with other genes) in different stages of *T. cruzi*. Total RNA and cDNA from the epimastigote (E), trypomastigote (T), and amastigote (A) forms of *T. cruzi* was obtained. The cDNA (2 µl) from each stage was subsequently amplified by PCR in a 50 µl reaction volume using 2.5 U of Taq polymerase and 1 _l of 20 _M gene-specific forward and reverse primers. Individual amplicons were electrophoresed on 1% agarose gel, and imaged. GAPDH and GPI8 genes that are constitutively expressed in all three stages of *T. cruzi* were used as positive control (FIG. 6A). These data demonstrated that TcG1, TcG2, and TcG4 are expressed in epimastigote and amastigote stages and TcG1 and TcG4 are also expressed in trypomastigote stage of *T. cruzi [*31].

Example 10

Figure 6B:
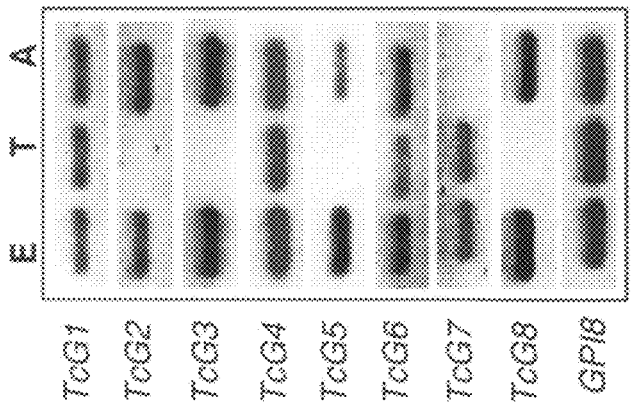
Figure 6A:
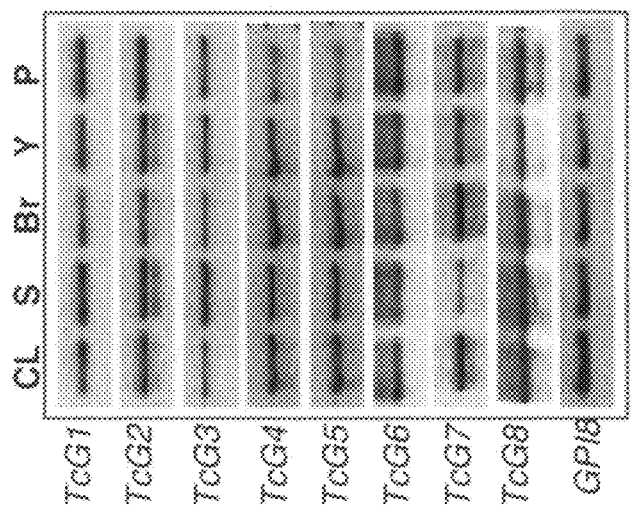

TcG1, TcG2, and TcG4 Encoding Sequences are Present in Diverse Strains of T. cruzi Genomic DNA was isolated from different T. cruzi strains obtained from endemic countries. Briefly, parasites were lysed in lysis buffer (50 mM Tris-HCl, pH 8, 62.5 mM EDTA, 2.5 M LiCl, 4% (v/v) Triton X-100) ($10^9$ parasites/ml). Samples were extracted with an equal volume of phenol: chloroform:isoamylalcohol (24:24:1), centrifuged at 12,000 g for 5 min, and the total DNA in top aqueous phase purified by ethanol precipitation. PCR amplification was then carried out of the selected genes for 35 cycles in a 50 µl reaction volume with 100 ng of genomic DNA and 1 _l of 20 _M gene-specific forward and reverse primers. PCR amplified products were resolved by agarose gel electrophoresis, and imaged (FIG. 6B). These data demonstrate that TcG1, TcG2, and TcG4 are phylogenetically conserved in CL Brenner (CL), Sylvio X10 (S), Brazil (Br), Y strain of T. cruzi (P: plasmid DNA used as control). Genomic DNA from Leishmania major and Trypanosoma brucei were used as template in parallel reactions. TcG1, TcG2 and TcG4 were not amplified in genomic DNA of Leishmania and Trypanosoma brucei, thus establishing their specificity to T. cruzi [31].

Example 11

TcG1, TcG2, TcG4 Elicit Antigen-Specific Antibody Response in Mice

C57BL/6 mice (8/group) were immunized with pCDNA3 eukaryotic expression plasmids encoding TcG1, TcG2, and TcG4 followed by recombinant proteins generated in E. coli (named TcVac2). Sera were collected 2-weeks after second immunization, and an enzyme-linked immunosorbent assay (ELISA) was performed. Briefly, 96-well plates were coated with recombinant antigen (20 µg/ml, 50 µl/well) or T. cruzi lysate (TcTL) (50% trypomastigotes/50% amastigotes, $10^9$/ml, 50 µl/well), blocked with 5% non-fat dry milk. Plates were then sequentially incubated at room temperature with sera samples (1:50-1:1000 dilution, 50 µl/well) in triplicate, followed by appropriate HRP-conjugated secondary antibody (1:5000 dilution). All dilutions were made in PBST-0.5% NFDM. Color was developed with 100-µl/well Sure Blue TMB substrate (Kirkegaard & Perry Labs), reaction was stopped with 2N sulfuric acid, and antibody response was monitored at 450 nm using a Spectramax microplate reader (FIG. 7).

Figures 7A, 7B:
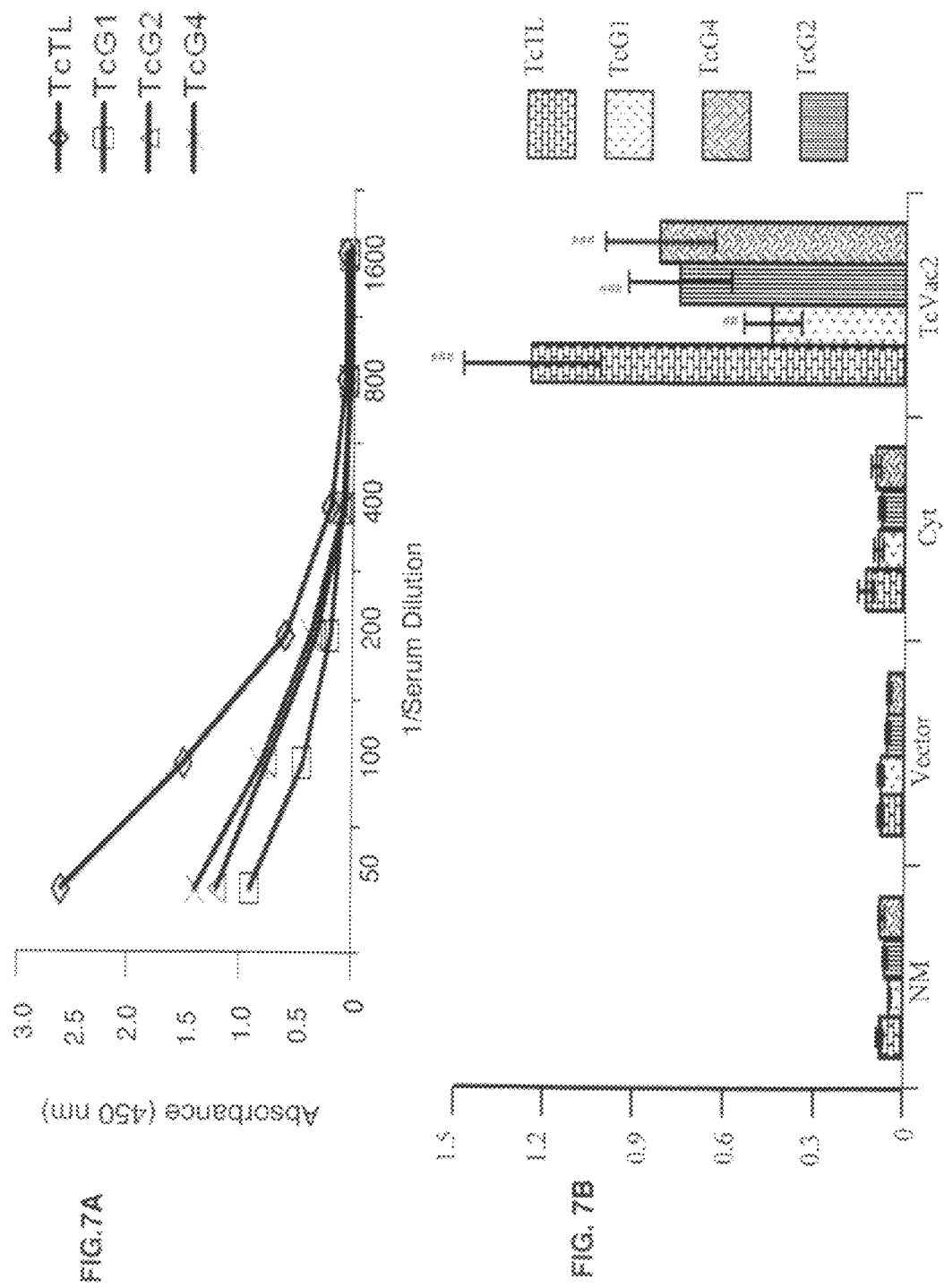

FIG. 7A shows the sera levels of parasite- and antigen-specific antibodies, measured two-weeks after the last immunization. Various sera dilutions were tested (1:50-1:1000) to identify maximum signal/noise ratio. FIG. 7B shows sera levels (1:100 dilution) of antibody response in normal mice (NM), and mice injected with pCNDA3 vector only (Vector), or cytokine (cyt) adjuvants only as control. TcVac2 is defined above. All data are presented as mean value from triplicate observations/sample (n=at least 6). Standard deviation is shown in FIG. 7B ($^{\#\#}p<0.001$).

These data demonstrate that TcG1, TcG2, and TcG4 are immunogenic in mice, and immune system of mice recognizes these proteins and elicit antigen-specific antibody response. The antigen-specific response was additive, and co-delivery of these antigens did not inhibit the immunogenicity of other antigens. These data also demonstrate the specificity of the antibodies against the three antigens.

Example 8

Figures 8A, 8B:
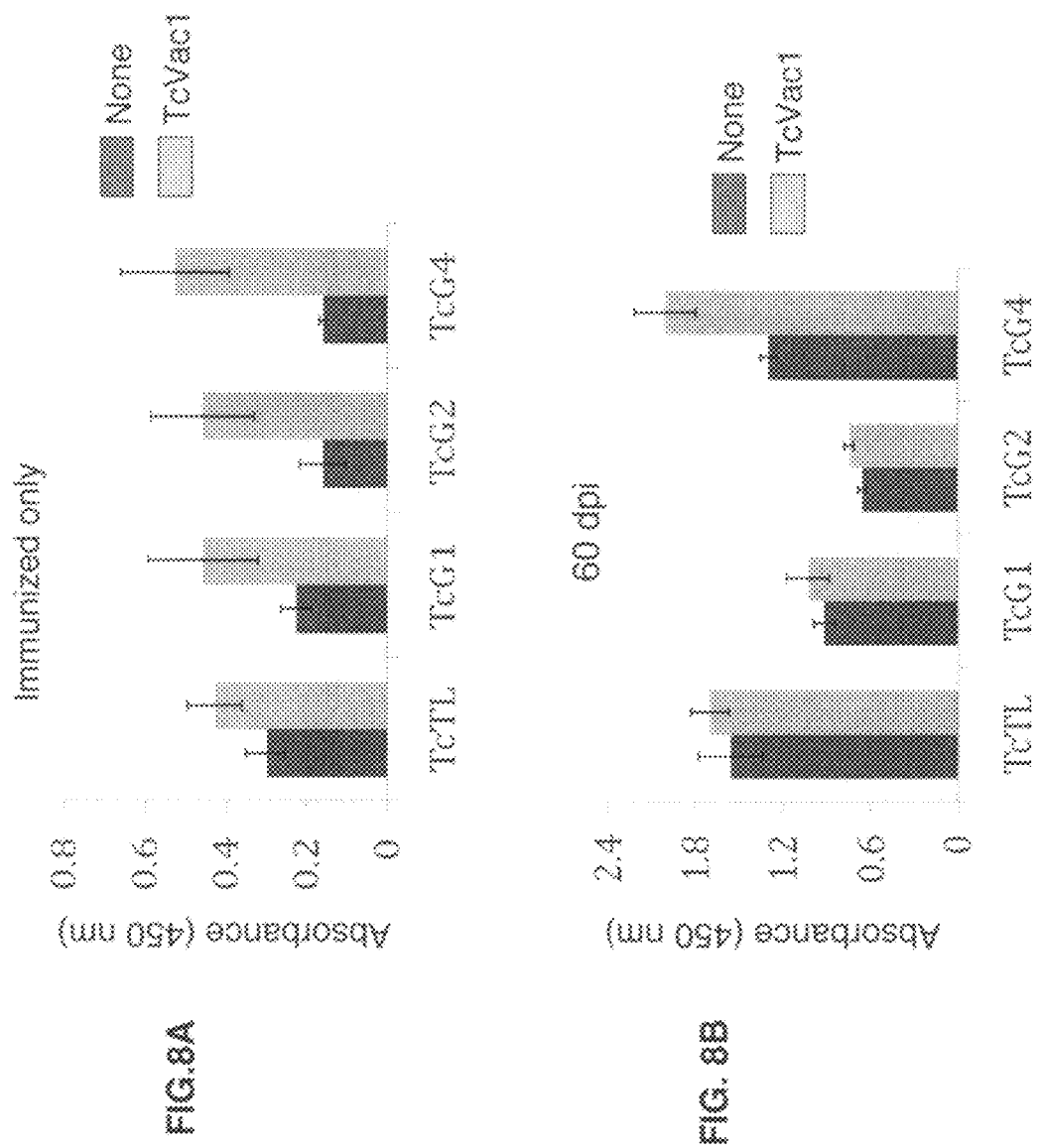
FIGS. 8A-8B depict that immunization with TcG1, TcG2, TcG4 elicits antigen-specific antibody response in dogs.

Immunization with TcG1, TcG2, TcG4 Elicits Antigen-Specific Antibody Response in Dogs As above, dogs (6/group) were immunized with TcG1, TcG2 and TcG4 (i.e., TcVac2). Sera were collected 2-weeks after immunization, and ELISA was performed using 1:50 dilution of sera samples (FIG. 8A). In some experiments, 2-weeks after immunization, dogs were infected with T. cruzi trypomastigotes and sera samples were collected at 60 days post-infection (FIG. 8B). Sera samples from naïve dogs and dogs experimentally or naturally infected with T. cruzi were used as controls. FIG. 8 shows sera level of antibodies in dogs immunized with candidate antigens (FIG. 8A) and infected with T. cruzi (FIG. 8B), measured by ELISA. The data demonstrate that TcG1, TcG2, and TcG4 are immunogenic in dogs, and antigen-specific antibody responses are elicited in dogs immunized with the candidate antigens (FIG. 8A). FIG. 8B shows that in response to infection with T. cruzi, both vaccinated and non-vaccinated dogs mount antibody response to T. cruzi antigenic lysate (TcTL) as well as to TcG1, TcG2 and TcG4 antigens. The detection of antigen-specific antibody responses in dogs infected by T. cruzi suggest the potential utility of these antigens in screening the prevalence of T. cruzi infection in dogs.

Example 9

Prevalence of Antibodies to TcG1, TcG2, and TcG4 in Sera Samples of Human Inhabitants Mexico: All samples came from clinics located in areas where triatomine infestation and the prevalence of T. cruzi was earlier reported. Samples were obtained from randomly selected adults. A total of 1481 human sera samples, collected from Chiapas, Mexico, were first analyzed by ELISA using T. cruzi lysate (TcTL) as antigen for IgG response (FIG. 9A). The 121 samples identified as seropositive using TcTL and an equivalent number of seronegative samples (randomly chosen) were then tested for TcG1-, TcG2-, and TcG4-specific IgG and IgM antibody response by ELISA.

FIG. 9 shows a box plot of ELISA data, graphically depicting the OD values for seronegative (gray box) and seropositive (white box) samples from Mexico, identified by ELISA. (FIG. 9A): IgG response, (FIG. 9B): IgM response. The standard deviation for triplicate observations for each sample was <12%. The horizontal lines of the box (bottom to top) depict the lower quartile (Q1, cuts off lowest 25% of the data); median (Q2, middle value); and upper quartile (Q3, cuts off the highest 25% of the data). The lower and upper whiskers depict the smallest and largest non-outlier observations, respectively, and solid dots represent the outliers. The spacing between the different parts of the box indicates the degree of dispersion (spread). The mean S.D. optical density (O.D.) value for the seronegative and serpositive populations was 0.44±0.19 and 1.64±0.45, respectively. An 8.5% seroprevalence for T. cruzi-specific IgG antibodies was identified in the inhabitants of Chiapas (n=121 out of 1481) using TcTL antigen. The 121 samples identified as seropositive using TcTL and an equivalent number of seronegative samples (randomly chosen) were then tested for TcG1-, TcG2-, and TcG4-specific IgG and IgM antibody response by ELISA. These data demonstrate that TcG1, TcG2 and TcG4 are equally or more effective in diagnosing the exposure to *T. cruzi* (FIG. 9A). Importantly TcG1-specific IgM antibodies were found to be >3-fold higher than the TcTL-specific IgM antibodies in seropositive patients, suggesting that TcG1 antigen is useful in detecting the early antibody responses, and possibly distinguish acute exposure to *T. cruzi*.

Figure 10:
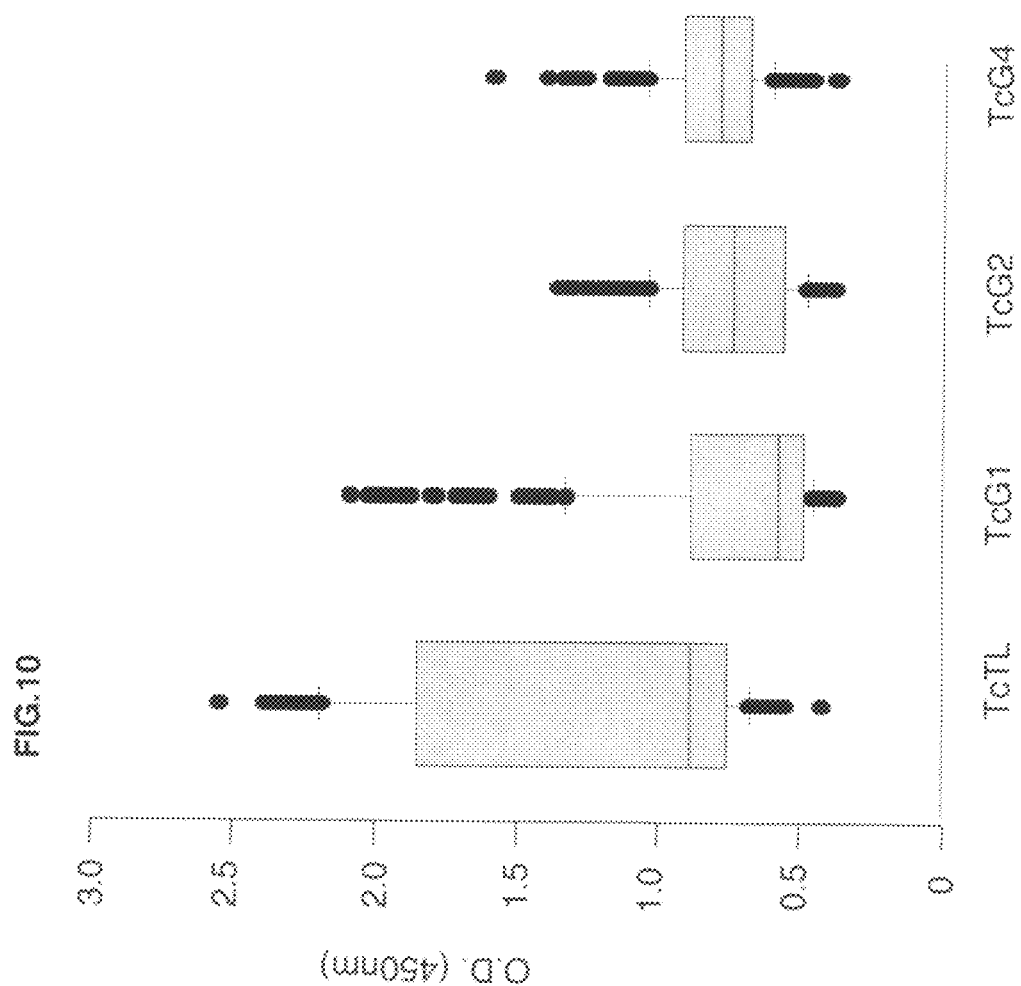
FIG. 10 depicts that TcG1-, TcG2- and TcG4-specific IgG antibodies are detected in sera of chagasic patients from Argentina. Over 300 sera samples, which were diagnosed as seropositive by commercially available kits, were analyzed to evaluate the antibody response to TcG1, TcG2, and TcG4 antigens.

Argentina: Over 300 sera samples, which were diagnosed as seropositive by commercially available kits, were analyzed to evaluate the antibody response to TcG1, TcG2, and TcG4 antigens. ELISA was performed using plates coated with the *T. cruzi* lysate or TcG1, TcG2 and TcG4 antigens. FIG. 10 demonstrates that TcG1-, TcG2- and TcG4-specific IgG antibodies are detected in sera of chagasic patients from Argentina.

The following references were cited herein:
1. Gurtler et al., (1990). *Ann Trop Med Parasitol* 84:313-323.
2. Gurtler et al. (1996). *Am J Trop Med Hyg* 55:24-31.
3. Guzman-Bracho C (2001). *Trends Parasitol* 17:372-376.
4. Barr et al. (1995). *Am J Vet Res* 56:1037-1044.
5. Bradley et al., (2000). *J Am Vet Med Assoc* 217:1853-1857.
6. Barnabe C, Yaeger R, Pung O, Tibayrenc M (2001) *Exp Parasitol* 99:73-79.
7. Meurs et al., (1998) *J Am Vet Med Assoc* 213:497-500.
8. Beard C B, Young D G, Butler J F, Evans D A (1988) *J Parasitol* 74:343-344.
9. Gurtler R E, Cohen J E, Cecere M C, Chuit R (1997) *J Appl Ecol* 34:699-715.
10. Cohen J E, Gurtler R E (2001) *Science* 293:694-698.
11. Moncayo A (2003) *Mem Inst Oswaldo Cruz* 98:577-591.
12. Garg N, Nunes M P, Tarleton R L (1997). *J Immunol* 158:3293-3302.
13. Wizel B, Nunes M, Tarleton R L (1997). *J Immunol* 159:6120-6130.
14. Low H P, Santos M A, Wizel B, Tarleton R L (1998) *J Immunol* 160:1817-1823.
15. Wizel B, Garg N, Tarleton R L (1998) *Infect Immun* 66:5073-5081.
16. Garg N, Tarleton R L (1998) In: Proceedings 10th International Congress of Immunology, New Delhi, India, p 1421-1426
17. Garg N, Tarleton R L (2002) *Infection & Immunity* 70:5547-5555.
18. Bhatia V, Sinha M, Luxon B, Garg N (2004) *Infect Immun* 72:6245-6254.
19. Bhatia V, Garg N J (2008) *Clin Vaccine Immunol* 15:1158-1164.
20. Sepulveda et al., (2000) *Infect Immun* 68:4986-4991.
21. Umekita L F, Mota I (2000) *Braz J Med Biol Res* 33:253-258.
22. Schofield C J, Jannin J, Salvatella R (2006) *Trends Parasitol*, 22, 583-588.
23. World Health Organization (2006) Technical, UNDP/World Bank/WHO.
24. World Health Organization (2010) Technical, UNDP/World Bank/WHO.
25. Bern C, Montgomery, S P (2009) *Clin Infect Dis*, 49, e52-54.
26. Weinberg et al. (2003) *Emerg Infect Dis*, 9, 97-102.
27. Garraud et al., (2007) *Travel Med Infect Dis*, 5, 110-112.
28. CDC (2006) *MMWR Morb Mortal Wkly Rep*, 55, 798-800.
29. CDC (2007) *MMWR Morb Mortal Wkly Rep*, 56, 141-143.
30. Rodriques-Coura J, de Castro S L (2002) *Mem Inst Oswaldo Cruz*, 97, 3-24.
31. Bhatia V, Sinha M, Luxon B, Garg N (2004) *Infect Immun*, 72, 6245-6254.

Any patents or publications mentioned in this specification are indicative of the levels of those skilled in the art to which the invention pertains. These patents and publications are herein incorporated by reference to the same extent as if each individual publication was specifically and individually incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A method for detecting *Trypanosoma cruzi* infection in a subject, said method comprising the steps of:

contacting a sample from a subject that has not been administered a vaccine comprising a *Trypanosoma cruzi* TcG-1 protein, a *Trypanosoma cruzi* TcG-2 protein, or a *Trypanosoma cruzi* TcG-4 protein with a composition comprising an isolated *Trypanosoma cruzi* TcG-1 protein, an isolated *Trypanosoma cruzi* TcG-2 protein, or an isolated *Trypanosoma cruzi* TcG-4 protein; and detecting binding of antibody in the sample to the isolated *Trypanosoma cruzi* TcG-1 protein, the isolated *Trypanosoma cruzi* TcG-2 protein, or the isolated *Trypanosoma cruzi* TcG-4 protein, wherein detection of antibody binding to the *Trypanosoma cruzi* protein(s) indicates that the subjected is infected with *Trypanosoma cruzi*.

2. The method of claim 1, wherein the antibody is IgG antibody.

3. The method of claim 1, wherein the antibody is IgM antibody.

4. The method of claim 1, wherein said sample is a serum or a blood sample.

5. The method of claim 1, wherein the sample is contacted with the *Trypanosoma cruzi* TcG-1 protein, the *Trypanosoma cruzi* TcG-2 protein, and the *Trypanosoma cruzi* TcG-4 protein.

6. A kit for detecting *Trypanosoma cruzi* infection comprising:
   (a) an isolated *Trypanosoma cruzi* TcG-1 protein, *Trypanosoma cruzi* TcG-2 protein, or *Trypanosoma cruzi* TcG-4 protein coupled to a substrate; and
   (b) a detection reagent.

7. The kit of claim 6, wherein
   the *Trypanosoma cruzi* TcG-1 protein has the amino acid sequence of SEQ ID NO: 2;
   the *Trypanosoma cruzi* TcG-2 protein has the amino acid sequence of SEQ ID NO: 3;
   the *Trypanosoma cruzi* TcG-4 protein has the amino acid sequence of SEQ ID NO: 5.

8. The kit of claim 6, wherein the substrate is a dip stick.

* * * * *

SEQUENCE LISTING

```
<160> NUMBER OF SEQ ID NOS: 27

<210> SEQ ID NO 1
<211> LENGTH: 647
<212> TYPE: PRT
<213> ORGANISM: Trypanosoma cruzi

<400> SEQUENCE: 1

Pro Cys Glu Ala Ala Asp Ala Val Glu Gly Lys Ser Gly Ala Val Gln
1               5                   10                  15

Leu Pro Lys Trp Val Asp Ile Phe Val Pro Glu Lys Thr His Val Leu
            20                  25                  30

Pro Lys Glu Gly Ser Glu Ser Gly Val Lys Lys Ala Phe Ala Ala Pro
        35                  40                  45

Ser Leu Val Ser Ala Gly Gly Val Met Val Ala Phe Ala Glu Gly Phe
    50                  55                  60

Ser Glu Tyr Asn Ala His Glu Asn Asn Pro Phe Gly Ile Arg Pro Tyr
65                  70                  75                  80

Glu Ile Leu Ala Gly Tyr Ile Lys Ala Ala Glu Ser Trp Pro Ser Ile
```

```
                        85                  90                  95
Val Ala Glu Val Asn Ala Ser Thr Trp Arg Ala His Thr Val Ile Gly
                100                 105                 110

Ser Arg Asn Gly Asn Asp Arg Leu Cys Phe Leu Tyr Arg Pro Thr Ala
            115                 120                 125

Val Ala Arg Glu Asn Lys Val Phe Leu Leu Val Gly Ser Asp Thr Val
        130                 135                 140

Gly Tyr Asp Ser Asp Asp Met Trp Val Lys Asp Gly Trp Asp Ile
145                 150                 155                 160

Gln Leu Val Glu Gly Val Ala Thr Gln Ser Thr Asp Gly Lys Pro Ser
                165                 170                 175

Lys Thr Ile Asn Trp Gly Glu Pro Lys Ser Leu Leu Lys His Ile Pro
            180                 185                 190

Lys His Thr Gln Gly His Leu Arg Asp Val Val Thr Ala Gly Gly Ser
        195                 200                 205

Gly Ile Val Met Gln Asn Asn Thr Leu Val Phe Pro Leu Val Val Asn
210                 215                 220

Gly Lys Asn Tyr Pro Phe Ser Ser Ile Thr Tyr Ser Thr Asp Asn Gly
225                 230                 235                 240

Asn Asn Trp Val Phe Pro Glu Ser Ile Ser Pro Val Gly Cys Leu Asp
                245                 250                 255

Pro Arg Ile Thr Glu Trp Glu Thr Gly Gln Ile Leu Met Ile Val Asp
            260                 265                 270

Cys Gly Asn Gly Gln Ser Val Tyr Glu Ser Arg Asp Met Gly Thr Thr
        275                 280                 285

Trp Thr Lys Ala Val Arg Thr Leu Ser Gly Val Trp Ala Ile Ser Gln
290                 295                 300

Arg Gly Val Arg Ser Tyr Glu Ile Phe Arg Val Gly Ala Ile Ile Thr
305                 310                 315                 320

Ala Thr Ile Glu Gly Arg Lys Val Met Leu Tyr Thr Arg Arg Gly Tyr
                325                 330                 335

Ala Ser Gly Glu Lys Glu Ala Asn Ala Leu Tyr Leu Trp Val Thr Asp
            340                 345                 350

Asn Asn Arg Thr Phe His Val Gly Pro Val Ala Met Asp Ser Ala Val
        355                 360                 365

Asn Glu Thr Leu Ser Asn Ala Leu Leu Tyr Ser Asp Gly Asn Leu His
370                 375                 380

Leu Leu Gln Gln Arg Ala Asn Glu Lys Gly Ser Ala Ile Ser Leu Ala
385                 390                 395                 400

Arg Leu Thr Glu Glu Leu Lys Glu Ile Glu Ser Val Leu Arg Thr Trp
                405                 410                 415

Ala Gln Leu Asp Ala Phe Phe Ser Lys Ser Thr Pro Thr Ala Gly
            420                 425                 430

Leu Val Gly Phe Leu Ser Asn Thr Ser Ser Gly Gly Asn Thr Trp Ile
        435                 440                 445

Asp Glu Tyr Arg Cys Val Asn Ala Thr Val Thr Lys Ala Ser Lys Val
450                 455                 460

Lys Asn Gly Phe Lys Phe Thr Gly Pro Gly Pro Met Ala Thr Trp Leu
465                 470                 475                 480

Val Asn Ser Arg Glu Asp Asn Arg Gln Tyr Ser Phe Val Asn His Arg
                485                 490                 495

Phe Thr Leu Val Ala Thr Val Thr Ile His Gln Val Pro Lys Gly Ser
            500                 505                 510
```

```
Thr Pro Leu Leu Gly Ala Gly Leu Gly Asp Gly His Gly Ala Lys Ile
            515                 520                 525

Ile Gly Leu Ser Tyr Ser Met Asn Lys Thr Trp Glu Thr Val Phe Tyr
    530                 535                 540

Gly Lys Lys Thr Thr Ser Asn Thr Thr Trp Glu Leu Gly Lys Glu Tyr
545                 550                 555                 560

Gln Val Thr Leu Met Leu Gln Asp Gly Asn Lys Gly Ser Val Tyr Val
                565                 570                 575

Asp Gly Val Ile Val Gly Ser Pro Ala Lys Ile Pro Lys Val Gly Ala
                580                 585                 590

Leu Gly His Glu Ile Ala His Phe Tyr Phe Gly Gly Glu Gly Asp
            595                 600                 605

Ser Asp Ser Ser Val Thr Val Thr Asn Val Phe Leu Tyr Asn Arg Pro
            610                 615                 620

Leu Ser Val Gly Glu Leu Lys Met Val Arg Lys Ser Asp Lys Lys
625                 630                 635                 640

Gly Asn Gly Gly Asp Gln Lys
                645

<210> SEQ ID NO 2
<211> LENGTH: 166
<212> TYPE: PRT
<213> ORGANISM: Trypanosoma cruzi

<400> SEQUENCE: 2

Met Val Lys Ala Asn Tyr Ile Arg Ala Gly Arg Leu Val Arg Ile Ile
1               5                   10                  15

Arg Gly Pro Arg Gln Asp Arg Val Gly Val Val Asp Ile Ile Asp
            20                  25                  30

Gly Asn Arg Val Leu Val Glu Asn Pro Ala Asp Lys Lys Met Trp Arg
        35                  40                  45

His Val Gln Asn Leu Lys Asn Val Glu Pro Leu Lys Phe Ser Val Glu
    50                  55                  60

Leu Ser Arg Asn Cys Ser Thr Arg Thr Leu Lys Asn Val Leu Ala Glu
65                  70                  75                  80

Lys Lys Ile Leu Glu Lys Tyr Ala Ala Thr Lys Ser Ala Arg Ile
                85                  90                  95

Ala Ala Lys Arg Ala Phe Ala Arg Ser Thr Asp Phe Glu Arg Tyr Gln
            100                 105                 110

Leu Arg Val Ala Lys Arg Ser Arg Ala Phe Trp Thr Arg Lys Val Phe
        115                 120                 125

Asp Glu Asn Asp Gln Lys Lys Pro Val Ser Trp His Lys Val Ala Leu
    130                 135                 140

Lys Lys Leu Gln Lys Asn Ala Lys Lys Val Asp Ser Lys Pro Ala Ala
145                 150                 155                 160

Lys Lys Arg Ile Ser Asn
                165

<210> SEQ ID NO 3
<211> LENGTH: 221
<212> TYPE: PRT
<213> ORGANISM: Trypanosoma cruzi

<400> SEQUENCE: 3

Met Ser Leu Ser Phe Ile Glu Ser Gly Phe Val Pro Ser Asp Gly Met
1               5                   10                  15
```

```
Arg Arg Gly Val Glu Ala Ala Asp Thr Ser Ala Ala Glu Leu Leu
            20                  25                  30

His Leu Ala Val Pro Pro Leu Met Asp Ala Gly Gly Lys Thr Arg Val
            35                  40                  45

Cys Val Ala Phe Tyr Glu Ala Ala Gln Cys Pro Phe Asp Ser Arg Cys
 50                  55                  60

Glu His Ala His His Phe Ser Glu Leu Asn Gly Tyr Thr Gln Asn Lys
 65                  70                  75                  80

Leu Leu Glu Thr Val Pro Val Glu Ser Ile Pro Lys His Phe Val Ala
                85                  90                  95

Pro Leu Asn Ser Asn Ser Ser Gly Asn Asn Lys Asn Asp Arg Thr
            100                 105                 110

Phe Tyr Ala Thr Asp Gly Asn Ala Ala Asn Tyr Thr Ala Thr Ala Ala
            115                 120                 125

Val Asp Gly Gly Val Ala His Arg Ser Leu Gly Gly Glu His Gly Glu
130                 135                 140

Lys Glu Lys Thr Ser Thr Asn Arg Arg Ser Lys Arg Thr Ala Arg Leu
145                 150                 155                 160

Tyr Asp Ile Ser Gly Ser Asn Thr Asn Leu Cys Asp Asn Ser Leu Ser
                165                 170                 175

Ser Leu Ala Ser Ser Thr Asp Thr Leu Leu Leu Gly Ser Val His
            180                 185                 190

Asp Ser Lys Asp Val Ser Pro Gln Lys Gly Thr Arg Arg Asp Glu Gly
            195                 200                 205

Met Glu Ala Phe Arg Ile Arg Leu Pro Pro Leu Leu Gly
210                 215                 220

<210> SEQ ID NO 4
<211> LENGTH: 336
<212> TYPE: PRT
<213> ORGANISM: Trypanosoma cruzi

<400> SEQUENCE: 4

Met Leu Gln Arg Thr Cys Ser Gly Ser Leu Tyr Ala Val Leu Glu Val
 1               5                  10                  15

Ala Arg Asp Ala Thr Pro Gln Glu Ile Lys Lys Ala Tyr His Arg Leu
            20                  25                  30

Ala Leu Arg Leu His Pro Asp Lys Thr Gly Thr Thr Thr Glu Gln
            35                  40                  45

Phe Thr Leu Ile Gln Glu Ala Gln Ser Ile Leu Gly Asp Pro Arg Gln
 50                  55                  60

Arg Arg Val Tyr Asp Thr Phe Gly Arg Met Gly Ile Glu Ser Leu Arg
 65                  70                  75                  80

Gln Phe Gly Asp Gly Met Val Val Met Thr Thr Ala Gly Ile Arg Cys
                85                  90                  95

Ala Phe Phe Ile Ile Ala Phe Trp Met Leu Leu Trp Leu Leu Thr Leu
            100                 105                 110

Val Leu Ala Ile Val Arg Phe Asp Tyr Asn Lys Gly Trp Pro Trp Ala
            115                 120                 125

Ala Val Phe Ala Pro Val Trp Val Ala Leu Val Pro Leu Leu Leu Ile
130                 135                 140

Gly Gly Leu Leu Val Phe His Gly Ala Thr Arg Arg Glu Ile Ala Ser
145                 150                 155                 160

Thr Leu Leu Gly Leu Met Cys Phe Leu Val Thr Phe Ala Val Ala Met
```

```
                165                 170                 175
Phe Val Val Gly Leu Ser Gly Ala Leu Thr Trp Thr Ile Ala Leu Ala
            180                 185                 190

Pro Ser Ala Ala Ile Tyr Val Phe Gln Ser Cys Phe Ile Leu Arg Tyr
        195                 200                 205

Leu Leu Pro Phe Gln Phe Arg Asn Gly Phe Ala Glu Phe Ile Pro Pro
    210                 215                 220

Gly Ser Ser Val Cys Leu Ser Arg Met Tyr Trp Gly Phe Cys Trp Lys
225                 230                 235                 240

Gln Tyr Leu Lys Ser Cys Val Val Ser Ala Leu Leu Val Leu Pro Cys
                245                 250                 255

Tyr Arg Gly Ala Asn Arg Arg Gly Arg Tyr Ile Lys Thr Asp Leu Leu
            260                 265                 270

Leu Asp Ser Phe Tyr Ser Tyr Phe Val Leu Trp Val His Asp Val
        275                 280                 285

Cys Phe Cys Arg Thr Lys Ile Phe Cys Gly Asn Ser Gly Ala Val
    290                 295                 300

Met Ser Pro Glu Pro Thr Val Pro Cys Ala Asp Gly Arg His Arg Leu
305                 310                 315                 320

Arg Gln Ser Ser Phe Tyr Gly Met His Val Gly Gly Glu Val Ser Ser
                325                 330                 335

<210> SEQ ID NO 5
<211> LENGTH: 91
<212> TYPE: PRT
<213> ORGANISM: Trypanosoma cruzi

<400> SEQUENCE: 5

Met Ser Ala Lys Ala Pro Pro Lys Thr Leu His Gln Val Arg Asn Val
1               5                   10                  15

Ala Tyr Ile Phe Ala Ala Trp Ala Gly Leu Gln Lys Gly Phe Ala Glu
            20                  25                  30

Lys Ser Ala Asn Asp Lys Met Trp Val Glu His Gln Arg Arg Leu Arg
        35                  40                  45

Gln Glu Asn Ala Lys Arg Gln His Ala Ala His Ala Leu Glu Glu Leu
    50                  55                  60

Lys Gln Asp Glu Glu Leu Glu Arg Ser Ile Pro Thr Ile Val Pro Lys
65                  70                  75                  80

Glu Leu His Glu Leu Val Lys Ala Leu Glu Lys
                85                  90

<210> SEQ ID NO 6
<211> LENGTH: 449
<212> TYPE: PRT
<213> ORGANISM: Trypanosoma cruzi

<400> SEQUENCE: 6

Met Gly Lys Glu Lys Val His Met Asn Leu Val Val Val Gly His Val
1               5                   10                  15

Asp Ala Gly Lys Ser Thr Ala Thr Gly His Leu Ile Tyr Lys Cys Gly
            20                  25                  30

Gly Ile Asp Ile Gly Lys Lys Arg Thr Ile Glu Lys Phe Glu Lys Glu
        35                  40                  45

Ala Ala Glu Ser Ser Phe Lys Tyr Ala Trp Val Leu Asp Lys Leu Lys
    50                  55                  60

Ala Glu Arg Glu Arg Gly Ile Thr Ile Asp Ile Ala Leu Trp Lys Phe
```

```
                65                  70                  75                  80
        Glu Ser Pro Lys Ser Val Phe Thr Ile Ile Asp Ala Pro Gly His Arg
                        85                  90                  95
        Asp Phe Ile Lys Asn Met Ile Thr Gly Thr Ser Gln Ala Asp Ala Ala
                        100                 105                 110
        Val Leu Val Ile Ala Ser Ser Gln Gly Glu Phe Glu Ala Gly Ile Ser
                        115                 120                 125
        Lys Asp Gly Gln Thr Arg Glu His Ala Leu Leu Ala Phe Thr Leu Gly
                        130                 135                 140
        Val Lys Gln Met Val Val Cys Cys Asn Lys Met Asp Asp Lys Ser Val
        145                 150                 155                 160
        Asn Phe Ala Gln Glu Arg Tyr Asp Glu Ile Val Lys Glu Val Ser Ala
                        165                 170                 175
        Tyr Leu Lys Lys Val Gly Tyr Asn Val Glu Lys Val Arg Phe Ile Pro
                        180                 185                 190
        Ile Ser Gly Trp Gln Gly Asp Asn Met Ile Asp Lys Ser Glu Asn Met
                        195                 200                 205
        Pro Trp Tyr Lys Gly Pro Thr Leu Leu Glu Ala Leu Asp Met Leu Glu
        210                 215                 220
        Pro Pro Val Arg Pro Ser Asp Lys Pro Leu Arg Leu Pro Leu Gln Asp
        225                 230                 235                 240
        Val Tyr Lys Ile Gly Gly Ile Gly Thr Val Pro Val Gly Arg Val Glu
                        245                 250                 255
        Thr Gly Thr Met Lys Pro Gly Asp Val Val Thr Phe Ala Pro Ala Asn
                        260                 265                 270
        Val Thr Thr Glu Val Lys Ser Ile Glu Met His His Glu Gln Leu Ala
                        275                 280                 285
        Glu Ala Thr Pro Gly Asp Asn Val Gly Phe Asn Val Lys Asn Val Ser
                        290                 295                 300
        Val Lys Asp Ile Arg Arg Gly Asn Val Cys Gly Asn Ser Lys Asn Asp
        305                 310                 315                 320
        Pro Pro Lys Glu Ala Ala Asp Phe Thr Ala Gln Val Ile Ile Leu Asn
                        325                 330                 335
        His Pro Gly Gln Ile Gly Asn Gly Tyr Ala Pro Val Leu Asp Cys His
                        340                 345                 350
        Thr Cys His Ile Ala Cys Lys Phe Ala Glu Ile Glu Ser Lys Ile Asp
                        355                 360                 365
        Arg Arg Ser Gly Lys Glu Leu Glu Lys Asn Pro Lys Ser Ile Lys Ser
                        370                 375                 380
        Gly Asp Ala Ala Met Val Arg Met Val Pro Gln Lys Pro Met Cys Val
        385                 390                 395                 400
        Glu Val Phe Asn Asp Tyr Ala Pro Leu Gly Arg Phe Ala Val Arg Asp
                        405                 410                 415
        Met Arg Gln Thr Val Ala Val Gly Ile Ile Lys Ala Val Thr Lys Lys
                        420                 425                 430
        Asp Gly Gly Ala Gly Lys Val Thr Lys Ala Ala Ala Lys Ala Ala Lys
                        435                 440                 445
        Lys

<210> SEQ ID NO 7
<211> LENGTH: 252
<212> TYPE: PRT
<213> ORGANISM: Trypanosoma cruzi
```

<400> SEQUENCE: 7

```
Met Gln Ser Glu Leu Ser Gly Ile Leu Ser Arg Ile Pro Ala Ala Val
1               5                   10                  15

Ile Gly Thr Ile Leu Ala Asp Glu Ser Cys Lys Thr Val Trp Phe Phe
            20                  25                  30

Asn Pro Lys Ser Arg Glu Val Ile Ser Met Asp Ala Leu Arg Ser Leu
        35                  40                  45

Pro Asn Pro Pro Ser Asn Ser Gly Ala Asp Ala Thr Glu Arg His Leu
    50                  55                  60

Val Tyr Gly Met Met Arg Val Arg Asn Gln Gly Val Met Phe Glu Arg
65                  70                  75                  80

Asp His Ile Gln Arg Leu Tyr Glu Asn Cys Val Leu Ala Ala Thr Ser
                85                  90                  95

Lys Pro Leu Thr Asp Glu Ala Thr Leu Pro Phe Pro Val Glu Gly Val
            100                 105                 110

Thr Gln Ser Ile Arg Glu Tyr Ile Leu Ser Glu His Lys Glu Ser Gly
        115                 120                 125

Asp Ile Asn Leu Lys Phe Val Thr Trp Leu Pro Pro Phe Ser Asn Ser
    130                 135                 140

Leu Thr Thr Ala Glu Ala Trp Gln Lys Phe Leu Ser Asp Phe Ser Tyr
145                 150                 155                 160

Val Val Tyr Phe Val Lys Ser Phe Phe Pro Pro Lys Glu Trp Tyr Thr
                165                 170                 175

Glu Gly Ile Arg Ile Ser Leu Leu Tyr Asn Ala Arg Arg His Thr Pro
            180                 185                 190

Asn Ala Lys Ile Ile Gln Ala Pro Leu Arg Ser Arg Ala Lys Ser Leu
        195                 200                 205

Gln Asp Ser Ser Gly Ala Phe Glu Val Phe Phe Val Trp Asp Lys Glu
    210                 215                 220

Ala His Phe Leu Val Pro Glu Gly Ser Arg Ser Asn Tyr Leu Leu Val
225                 230                 235                 240

Thr Glu Asp Gly His Leu Cys Cys Ser Leu Ala Val
                245                 250
```

<210> SEQ ID NO 8
<211> LENGTH: 116
<212> TYPE: PRT
<213> ORGANISM: Trypanosoma cruzi

<400> SEQUENCE: 8

```
Met Leu Ala Thr His Gly Arg Gly Arg Arg Val Gln Gly Ala Val Gly
1               5                   10                  15

Ala Val Phe Ser Phe Glu Glu Gly Lys Arg Gly Lys Thr Arg Arg Ala
            20                  25                  30

Pro Leu Thr Ser Gln Asn Ala Arg Lys Lys Thr Val Lys Ser Ile
        35                  40                  45

Ala Ala Ser Cys Gly Ala Asp Pro Asp Ile Leu His Glu Arg Asn Ser
    50                  55                  60

Thr Ala Leu Leu Lys Glu Gly Asp Gly Val Val Tyr Ser Ala Val Pro
65                  70                  75                  80

Lys Tyr Lys Gln Ser Arg Leu Gly Val Leu Leu Gln His Pro Leu Tyr
                85                  90                  95

Ser Pro His Val Val Cys Cys Arg Phe Val Cys Val Arg Leu Arg
            100                 105                 110
```

Arg Gly Trp Met
        115

<210> SEQ ID NO 9
<211> LENGTH: 395
<212> TYPE: PRT
<213> ORGANISM: Trypanosoma cruzi

<400> SEQUENCE: 9

Met Ser Asp Asn His Gln Leu Glu Tyr Lys Arg Gly Leu Glu Asp Ala
1               5                   10                  15

Arg Arg His Arg Ser Arg Thr Glu Asp Asn Trp Leu Arg Ala Ser Val
            20                  25                  30

Gly Pro Leu Leu Trp Phe Gly Val Pro Phe Ala Val Ala Trp Leu Tyr
        35                  40                  45

Leu Arg Arg Gln Ala Pro Ala Ser Ala Lys Ile Asn Pro Phe Gly Gly
    50                  55                  60

Met Met Glu Gln Met Met Pro Ile Lys Lys Arg Gln Phe Arg Val Asp
65                  70                  75                  80

Val Lys Gly Thr Lys Phe Glu Asp Val Ile Gly Ile Pro Glu Ala Lys
                85                  90                  95

Gln Glu Val Gln Gln Tyr Val Glu Phe Leu Thr Asn Pro Asn Lys Phe
            100                 105                 110

Thr Arg Leu Gly Ala Arg Leu Pro Lys Gly Arg Leu Leu Thr Gly Glu
        115                 120                 125

Pro Gly Thr Gly Lys Thr Leu Leu Ala Lys Ala Val Ala Gly Glu Ala
    130                 135                 140

Asp Val Pro Phe Phe Ser Cys Ser Gly Ser Asp Phe Ile Glu Leu Met
145                 150                 155                 160

Gly Gly Ser Gly Pro Lys Arg Val Arg Glu Leu Phe Glu Glu Ala Arg
                165                 170                 175

Ser Ser Ala Pro Ala Ile Val Phe Ile Asp Glu Ile Asp Ala Ile Gly
            180                 185                 190

Ser Arg Ala Gly Lys Ile Gly Gly Ser Val Ser Ser Glu Glu Asn Arg
        195                 200                 205

Thr Ile Asn Gln Leu Leu Ala Glu Leu Asp Gly Leu Asn Thr Gly Thr
    210                 215                 220

Asp Ala Ile Ile Val Ile Ala Ala Thr Asn Phe Gln Asp Asn Ile Asp
225                 230                 235                 240

Lys Ala Leu Leu Arg Glu Gly Arg Phe Asp Arg Lys Val Asn Ile Glu
                245                 250                 255

Met Pro Asp Lys Ala Ala Arg Val Asp Ile Phe Lys His Tyr Leu Asn
            260                 265                 270

Arg Val Gly Thr Gly Asp Pro Arg Gly Arg Lys Val Asp Glu Glu Gly
        275                 280                 285

Glu Pro Leu Pro Thr Asn Glu Lys Val Asp Asn Leu Glu Leu Ala Arg
    290                 295                 300

Glu Leu Ala Asp Leu Thr Pro Gly Val Ser Pro Ala Thr Ile Ala Thr
305                 310                 315                 320

Ile Val Asn Glu Ala Ala Leu Gln Ser Gly Ile Arg Glu Lys Arg Leu
                325                 330                 335

Val Asp Lys Glu Ser Ile Leu Glu Ala Val Asp Asn Thr Leu Val Gly
            340                 345                 350

Arg Lys His Arg Asn Arg Gln Ser Val Thr Ser Leu Arg Arg Thr Ala
        355                 360                 365

Ile His Glu Ala Gly His Ala Leu Thr Ala Trp Met Leu Pro Ser Val
    370                 375                 380

Lys Gln Val Leu Lys Val Ser Val Val Pro Gln
385                 390                 395

<210> SEQ ID NO 10
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 10
ggatccatgg tgaaggcgaa ctatatt                                    27

<210> SEQ ID NO 11
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 11
gggtctagat cacgttcgag atgcgcttc                                  29

<210> SEQ ID NO 12
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 12
ggatccatgt cgctttcatt tatcgagtca ggg                             33

<210> SEQ ID NO 13
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 13
gggtctagat cacccaacag cggtggaa                                   28

<210> SEQ ID NO 14
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 14
ggatccatgc ttcagcgtac ctgcagc                                    27

<210> SEQ ID NO 15
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 15
gggtctagat cagcttgaca cttcgc                                     26

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
ggatccatgt cagccaaggc tccc                                          24

<210> SEQ ID NO 17
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 17
gggtctagat cacttttcaa gcgcc                                         25

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
ggatccatgg ggaaggaaaa ggtgc                                         25

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 19
gggtctagat cacttcttag cggc                                          24

<210> SEQ ID NO 20
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 20
aaggctatgc tggcgacac                                                19

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 21
gggtctagat cacacagcaa ggg                                           23

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 22
ggatccatgc tggcgacaca cgg                                              23

<210> SEQ ID NO 23
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 23
gggtctagac tacatccatc ctcgcc                                           26

<210> SEQ ID NO 24
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 24
ggatccatgt ccgataacca tcaactgg                                         28

<210> SEQ ID NO 25
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 25
gggtctagat cactgtggta caacgctg                                         28

<210> SEQ ID NO 26
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 26
aagcttcgag cattgtctat gtgccttgaa                                       30

<210> SEQ ID NO 27
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 27
ctcgagctac agcaggtcat attgtacatc                                       30
```